US012740934B2

(12) United States Patent
Lan et al.

(10) Patent No.: US 12,740,934 B2
(45) **Date of Patent: *Sep. 22, 2026**

(54) AQUEOUS EMULSION BASED ANTIPERSPIRANT FORMULATION

(71) Applicants: Dow Global Technologies LLC, Midland, MI (US); Rohm and Haas Company, Collegeville, PA (US); Dow Silicones Corporation, Midland, MI (US)

(72) Inventors: Tian Lan, Langhorne, PA (US); Fanwen Zeng, Audubon, PA (US); Xiaodong Lu, North Wales, PA (US); Inna Shulman, Langhorne, PA (US); Isabelle Van Reeth, Incourt Walloon Brabant (BE); Fabienne Bizeray, Chambly (FR); Gregoire Cardoen, Collegeville, PA (US); Michaeleen Pacholski, Collegeville, PA (US); Peilin Yang, Pearland, TX (US); Helene Dihang, Taisnières-sur-Hon (FR); Marc Eeman, Sombreffe (BE); Tanvi S. Ratani, Pittsburgh, PA (US); Jason Fisk, Midland, MI (US); Tzu-Chi Kuo, Midland, MI (US)

(73) Assignees: Dow Global Technologies LLC, Midland, MI (US); ROHM AND HAAS COMPANY, Collegeville, PA (US); Dow Silicones Corporation, Midland, MI (US)

( * ) Notice: Subject to any disclaimer, the term of this patent is extended or adjusted under 35 U.S.C. 154(b) by 749 days.

This patent is subject to a terminal disclaimer.

(21) Appl. No.: 18/020,163

(22) PCT Filed: Sep. 2, 2021

(86) PCT No.: PCT/US2021/048776

§ 371 (c)(1),
(2) Date: Feb. 7, 2023

(87) PCT Pub. No.: WO2022/051441

PCT Pub. Date: Mar. 10, 2022

(65) Prior Publication Data

US 2023/0285268 A1 Sep. 14, 2023

Related U.S. Application Data

(60) Provisional application No. 63/074,015, filed on Sep. 3, 2020.

(51) Int. Cl.

| | |
|---|---|
| *A61K 8/81* | (2006.01) |
| *A61K 8/06* | (2006.01) |
| *A61K 8/26* | (2006.01) |
| *A61K 8/33* | (2006.01) |
| *A61K 8/39* | (2006.01) |
| *A61K 8/89* | (2006.01) |
| *A61K 8/92* | (2006.01) |
| *A61Q 15/00* | (2006.01) |

(52) U.S. Cl.

CPC .............. *A61K 8/8152* (2013.01); *A61K 8/06* (2013.01); *A61K 8/062* (2013.01); *A61K 8/064* (2013.01); *A61K 8/26* (2013.01); *A61K 8/33* (2013.01); *A61K 8/39* (2013.01); *A61K 8/8117* (2013.01); *A61K 8/8158* (2013.01); *A61K 8/8194* (2013.01); *A61K 8/89* (2013.01); *A61K 8/92* (2013.01); *A61Q 15/00* (2013.01)

(58) Field of Classification Search

None

See application file for complete search history.

(56) References Cited

U.S. PATENT DOCUMENTS

| | | | |
|---|---|---|---|
| 7,326,409 | B2 | 2/2008 | Lemoine et al. |
| 9,486,399 | B2 | 11/2016 | Zeng et al. |
| 11,976,144 | B2 | 5/2024 | Buss et al. |
| 2015/0290111 | A1 | 10/2015 | Fan et al. |
| 2017/0105923 | A1 | 4/2017 | Canfield et al. |
| 2017/0260393 | A1 | 9/2017 | Phukan et al. |

FOREIGN PATENT DOCUMENTS

| | | |
|---|---|---|
| WO | 2014083175 | 6/2014 |

*Primary Examiner* — Sin J Lee

(74) *Attorney, Agent, or Firm* — Thomas S. Deibert

(57) ABSTRACT

An aqueous antiperspirant composition is provided, comprising: (A) water; (B) a sweat repellent polymer, comprising a multistage polymer comprising: an acrylate rich stage comprising: structural units of a monoethylenically unsaturated nonionic acrylate rich stage monomer; and structural units of a first carbosiloxane monomer of formula (I); and a carbosiloxane rich stage, comprising: structural units of a vinyl monomer; and structural units of a second carbosiloxane monomer of formula (I); wherein the first carbosiloxane monomer of formula (I) and the second carbosiloxane monomer of formula (I) are the same or different; and (C) an antiperspirant aluminum salt; wherein the aqueous antiperspirant composition is an emulsion. Also provided are methods of using the same.

10 Claims, No Drawings

AQUEOUS EMULSION BASED ANTIPERSPIRANT FORMULATION

The present invention relates to an aqueous antiperspirant composition. In particular, the present invention relates to an aqueous antiperspirant composition comprising: (A) water; (B) a sweat repellent polymer, comprising a multistage polymer comprising: an acrylate rich stage comprising: structural units of a monoethylenically unsaturated nonionic acrylate rich stage monomer; and structural units of a first carbosiloxane monomer of formula (I); and a carbosiloxane rich stage, comprising: structural units of a vinyl monomer; and structural units of a second carbosiloxane monomer of formula (I); wherein the first carbosiloxane monomer of formula (I) and the second carbosiloxane monomer of formula (I) are the same or different; and (C) an antiperspirant aluminum salt; wherein the aqueous antiperspirant composition is an emulsion.

Antiperspirant products are widely used personal care products throughout the world. The primary benefit of these products is their ability to suppress perspiration and related odors on the body of the user. Antiperspirant products are applied to the skin and generally comprise an antiperspirant active which acts to inhibit excretion of perspiration.

It has long been desired to improve the efficacy of topical antiperspirant compositions in order that uses experience less perspiration wetness. Further, if the efficacy of such products can be improved, it may be possible to formulate products in which the concentration of the antiperspirant active component can be reduced while still providing products of equal or even higher efficacy. This could lead to such products being less expensive, easier to formulate, or generally having improved sensory and consumer perceived drynes sproperties. The present invention accomplishes this result, and als may permit the formulation of compositions which are aesthetically pleasing. This is accomplished by using a film forming material together with conventional antiperspirant actives.

The use of film-forming polymers in cosmetic and beauty care products is known in the art. Notwithstanding, there remains a need for new sweat repellent polymers that are effective film formers and that provide excellent sweat repellency and fragrance retention properties when formulated into aqueous antiperspirant compositions.

The present invention provides an aqueous antiperspirant composition, comprising: (A) water; (B) a sweat repellent polymer, wherein the sweat repellent polymer comprises a multistage polymer comprising: (a) an acrylate rich stage comprising: 38 to <100 wt %, based on weight of the acrylate rich stage, of structural units of a monoethylenically unsaturated nonionic acrylate rich stage monomer, wherein the monoethylenically unsaturated nonionic acrylate rich stage monomer is selected from the group consisting of $C_{1-22}$ alkyl (meth)acrylates and mixtures thereof; >0 to 50 wt %, based on weight of the acrylate rich stage, of structural units of a first carbosiloxane monomer of formula (I)

(I)

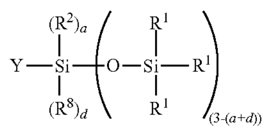

wherein a is 0 to 3; wherein d is 0 or 1; wherein each $R^1$ is independently selected from the group consisting of a hydrogen, a $C_{1-10}$ alkyl group and an aryl group; wherein each $R^2$ is independently selected from the group consisting of a hydrogen and a $C_{1-10}$ alkyl group; wherein each $R^8$ is a —O—Si$(CH_3)_3$ group; wherein Y is selected from the group consisting of formula (II), (III) and (IV)

(II)

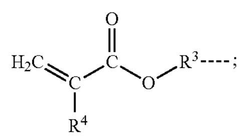

(III)

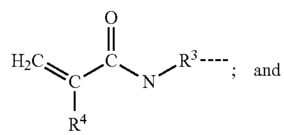

and (IV)

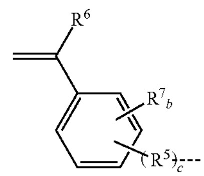

wherein each $R^4$ and $R^6$ are independently selected from the group consisting of a hydrogen and a methyl group; wherein each $R^3$ and $R^5$ are independently a $C_{1-10}$ alkylene group; wherein each $R^7$ is independently a $C_{1-10}$ alkyl group; wherein b is 0 to 4; wherein c is 0 or 1; 0 to 10 wt %, based on weight of the acrylate rich stage, of structural units of a monoethylenically unsaturated carboxylic acid acrylate rich stage monomer; and 0 to 2 wt %, based on weight of the acrylate rich stage, of structural units of a multiethylenically unsaturated acrylate rich stage monomer having at least two ethylenically unsaturated groups per molecule; and (b) a carbosiloxane rich stage, comprising: 0 to 90 wt %, based on weight of the carbosiloxane rich stage, of structural units of a vinyl monomer; and 10 to 100 wt %, based on weight of the carbosiloxane rich stage, of structural units of a second carbosiloxane monomer of formula (I); wherein the first carbosiloxane monomer of formula (I) and the second carbosiloxane monomer of formula (I) are the same or different; and (C) an antiperspirant aluminum salt; wherein the aqueous antiperspirant composition is an emulsion.

The present invention provides a method of inhibiting perspiration, comprising: providing water; providing an antiperspirant aluminum salt; selecting a sweat repellent polymer, wherein the sweat repellent polymer is selected to have a sweat contact angle of ≥30° and wherein the sweat repellent polymer comprises a multistage polymer comprising: (a) an acrylate rich stage comprising: 38 to <100 wt %, based on weight of the acrylate rich stage, of structural units of a monoethylenically unsaturated nonionic acrylate rich stage monomer, wherein the monoethylenically unsaturated nonionic acrylate rich stage monomer is selected from the group consisting of $C_{1-22}$ alkyl (meth)acrylates and mixtures thereof; >0 to 50 wt %, based on weight of the acrylate rich stage, of structural units of a first carbosiloxane monomer of formula (I); wherein a is 0 to 3; wherein d is 0 or 1; wherein each $R^1$ is independently selected from the group consisting of a hydrogen, a $C_{1-10}$ alkyl group and an aryl group; wherein each $R^2$ is independently selected from the group consisting of a hydrogen and a $C_{1-10}$ alkyl group; wherein each $R^8$ is a —O—Si$(CH_3)_3$ group; wherein Y is selected from the group consisting of formula (II), (III) and (IV); wherein each $R^4$ and $R^6$ are independently selected from the group consisting of a hydrogen and a methyl group; wherein each $R^3$ and $R^5$ are independently a $C_{1-10}$ alkylene group; wherein each $R^7$ is independently a $C_{1-10}$ alkyl group; wherein b is 0 to 4 and wherein c is 0 or 1; 0 to 10 wt %, based on weight of the acrylate rich stage, of structural units of a monoethylenically unsaturated carboxylic acid acrylate rich stage monomer; and 0 to 2 wt %, based on weight of the acrylate rich stage, of structural units of a multiethylenically unsaturated acrylate rich stage monomer having at least two ethylenically unsaturated groups per molecule; and (b) a carbosiloxane rich stage, comprising: 0 to 90 wt %, based on weight of the carbosiloxane rich stage, of structural units of a vinyl monomer; and 10 to 100 wt %, based on weight of the carbosiloxane rich stage, of structural units of a second carbosiloxane monomer of formula (I); wherein the first carbosiloxane monomer of formula (I) and the second carbosiloxane monomer of formula (I) are the same or different; providing the selected sweat repellent polymer; combining the water, the antiperspirant aluminum salt and the selected sweat repellent polymer to form an aqueous antiperspirant composition; wherein the aqueous antiperspirant composition is an emulsion; and applying the aqueous antiperspirant composition on skin to form a film.

DETAILED DESCRIPTION

We have surprisingly found multistage polymers comprising an acrylate rich stage and a carbosiloxane rich stage act as effective sweat repellent polymers (imparting aqueous antiperspirant compositions with excellent sweat repellency (i.e., a sweat contact angle ≥30°) and fragrance retention when formulated into emulsion based aqueous antiperspirant compositions comprising antiperspirant aluminum salts.

Unless otherwise indicated, ratios, percentages, parts, and the like are by weight.

The term "structural units" as used herein and in the appended claims refers to the remnant of the indicated monomer in a given polymer; thus a structural unit of ethyl acrylate is illustrated:

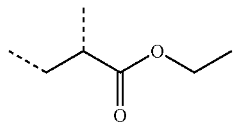

where the dotted lines represent the points of attachment to the polymer backbone.

The term "(meth)acrylic acid" as used herein and in the appended claims is intended to serve as a generic expression embracing both acrylic acid and methacrylic acid.

The term "(meth)acrylate" as used herein and in the appended claims is intended to serve as a generic expression embracing both acrylate and methacrylate.

The term "dermatologically acceptable" as used herein and in the appended refers to ingredients that are typically used for topical application to the skin, and is intended to underscore that materials that are toxic when present in the amounts typically found in skin care compositions are not contemplated as part of the present invention.

Preferably, the aqueous antiperspirant composition of the present invention is selected from the group consisting of a water-in-oil emulsion and an oil-in-water emulsion. More preferably, the aqueous antiperspirant composition of the present invention is selected from the group consisting of a water-in-oil emulsion and an oil-in-water emulsion deliverable from a roll-on applicator, a pump spray container, a tube or as a soft solid.

Preferably, the aqueous antiperspirant composition of the present invention, comprises: (A) water (preferably, 25 to 95.5 wt % (more preferably, 30 to 90 wt %; still more preferably, 40 to 85 wt %; most preferably, 45 to 80 wt %), based on weight of the aqueous antiperspirant composition, of the water); (B) a sweat repellent polymer (preferably, 0.1 to 10 wt % (more preferably, 0.5 to 8 wt %; still more preferably, 1 to 7 wt %; most preferably, 1.5 to 3 wt %), based on weight of the aqueous antiperspirant composition, of the sweat repellent polymer)(preferably, wherein the sweat repellent polymer is an emulsion polymer), wherein the sweat repellent polymer is a multistage polymer comprising: (a) an acrylate rich stage (preferably, 60 to 95 wt %; more preferably, 65 to 90 wt %; still more preferably, 70 to 85 wt %; most preferably, 75 to 82 wt %), based on weight of the multistage polymer, of the acrylate rich stage); wherein the acrylate rich stage comprises: 38 to <100 wt % (preferably, 44 to 99.39 wt %; more preferably, >77 to 98.73 wt %; still more preferably, 78.9 to 97.95 wt %; most preferably, 82.17 to 94.68 wt %), based on weight of the acrylate rich stage, of structural units of a monoethylenically unsaturated nonionic acrylate rich stage monomer, wherein the monoethylenically unsaturated nonionic acrylate rich stage monomer is selected from the group consisting of $C_{1-22}$ alkyl (meth)acrylates and mixtures thereof; >0 to 50 wt % (preferably, 0.1 to 50 wt %; more preferably, 0.5 to <20 wt %; still more preferably, 1 to 19 wt % most preferably, 4 to 16 wt %), based on weight of the acrylate rich stage, of structural units of a first carbosiloxane monomer of formula (I)

(I)

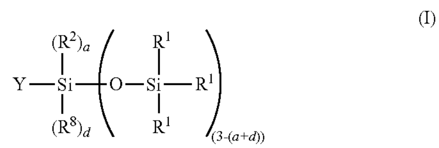

wherein a is 0 to 3 (preferably, 0 to 2; most preferably, 1); wherein d is 0 or 1 (preferably, 0); wherein each $R^1$ is independently selected from the group consisting of a hydrogen, a $C_{1-10}$ alkyl group and an aryl group (preferably, a hydrogen and a $C_{1-10}$ alkyl group; more preferably, a hydrogen and a $C_{1-4}$ alkyl group; still more preferably, a hydrogen and a methyl group; most preferably, a methyl group); wherein each $R^2$ is independently selected from the group consisting of a hydrogen and a $C_{1-10}$ alkyl group (preferably, a hydrogen and a $C_{1-5}$ alkyl group; more preferably, a hydrogen and a $C_{1-4}$ alkyl group; still more preferably, a hydrogen and a methyl group; most preferably, a methyl group); wherein each $R^8$ is a —O—$Si(CH_3)_3$ group; wherein Y is selected from the group consisting of formula (II), (III) and (IV) (preferably, (II) or (III); most preferably, (II))

(II)

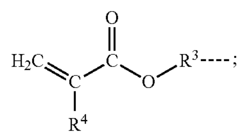

-continued (III)

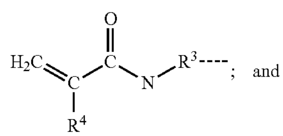

; and (IV)

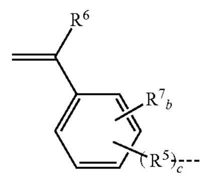

wherein each $R^4$ and $R^6$ are independently selected from the group consisting of a hydrogen and a methyl group (preferably, a methyl group); wherein each $R^3$ and $R^5$ are independently a $C_{1-10}$ alkylene group (preferably, a $C_{1-7}$ alkylene group; more preferably, a $C_{2-6}$ alkylene group; still more preferably, a $C_{3-5}$ alkylene group; most preferably, a $C_3$ alkylene group (e.g., $—CH_2—CH_2—CH_2—$)); wherein each $R^7$ is independently a $C_{1-10}$ alkyl group; wherein b is 0 to 4; wherein c is 0 or 1; 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid acrylate rich stage monomer; and 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated acrylate rich stage monomer having at least two ethylenically unsaturated groups per molecule; and (b) a carbosiloxane rich stage (preferably, 5 to 40 wt %; more preferably, 10 to 35 wt %; still more preferably, 15 to 30 wt %; most preferably, 18 to 25 wt %), based on weight of the multistage polymer, of the carbosiloxane rich stage), comprising: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; and 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a second carbosiloxane monomer of formula (I); wherein the first carbosiloxane monomer of formula (I) and the second carbosiloxane monomer of formula (I) are the same or different (preferably, wherein the first carbosiloxane monomer of formula (I) and the second carbosiloxane monomer of formula (I) are the same)(preferably, wherein the multistage polymer is an emulsion polymer)(more preferably, wherein the multistage polymer is an emulsion polymer, comprising an acrylate rich stage as a first stage and a carbosiloxane rich stage as a second stage); and (C) an antiperspirant aluminum salt (preferably, 0.1 to 35 wt % (preferably, 0.5 to 30 wt %; more preferably, 1 to 25 wt %; most preferably, 1.5 to 20 wt %), based on weight of the aqueous antiperspirant composition, of the antiperspirant aluminum salt); wherein the aqueous antiperspirant composition is an emulsion.

Preferably, the aqueous antiperspirant composition of the present invention, comprises (preferably, 25 to 95.5 wt % (more preferably, 30 to 90 wt %; still more preferably, 40 to 85 wt %; most preferably, 45 to 80 wt %), based on weigh of the aqueous antiperspirant composition, of water. More preferably, the aqueous antiperspirant composition of the present invention, comprises (preferably, 25 to 95.5 wt % (more preferably, 30 to 90 wt %; still more preferably, 40 to 85 wt %; most preferably, 45 to 80 wt %), based on weigh of the aqueous antiperspirant composition, of water; wherein the water is deionized, distilled or deionized and distilled. Most preferably, the aqueous antiperspirant composition of the present invention, comprises (preferably, 25 to 95.5 wt % (more preferably, 30 to 90 wt %; still more preferably, 40 to 85 wt %; most preferably, 45 to 80 wt %), based on weigh of the aqueous antiperspirant composition, of water; wherein the water is deionized.

Preferably, the aqueous antiperspirant composition of the present invention comprises 0.1 to 10 wt % (preferably, 0.5 to 8 wt %; more preferably, 1 to 7 wt %; most preferably, 1.5 to 3 wt %), based on weight of the aqueous antiperspirant composition, of a sweat repellent polymer. More preferably, the aqueous antiperspirant composition of the present invention comprises 0.1 to 10 wt % (preferably, 0.5 to 8 wt %; more preferably, 1 to 7 wt %; most preferably, 1.5 to 3 wt %), based on weight of the aqueous antiperspirant composition, of a sweat repellent polymer; wherein the sweat repellent polymer is a multistage polymer. Most preferably, the aqueous antiperspirant composition of the present invention comprises 0.1 to 10 wt % (preferably, 0.5 to 8 wt %; more preferably, 1 to 7 wt %; most preferably, 1.5 to 3 wt %), based on weight of the aqueous antiperspirant composition, of a sweat repellent polymer; wherein the sweat repellent polymer is a multistage polymer; and wherein the sweat repellent polymer is an emulsion polymer.

Preferably, the multistage polymer comprises an acrylate rich stage. More preferably, the multistage polymer, comprises: 60 to 95 wt % (preferably, 65 to 90 wt %; more preferably, 70 to 85 wt %; most preferably, 75 to 82 wt %), based on weight of the multistage polymer, of an acrylate rich stage. Most preferably, the multistage polymer, comprises 60 to 95 wt % (preferably, 65 to 90 wt %; more preferably, 70 to 85 wt %; most preferably, 75 to 82 wt %), based on weight of the multistage polymer, of an acrylate rich stage; wherein the acrylate rich stage, comprises: 38 to <100 wt % (preferably, 44 to 99.39 wt %; more preferably, >77 to 98.73 wt %; still more preferably, 78.9 to 97.95 wt %; most preferably, 82.17 to 94.68 wt %), based on weight of the acrylate rich stage, of structural units of a monoethylenically unsaturated nonionic acrylate rich stage monomer; wherein the monoethylenically unsaturated nonionic acrylate rich stage monomer is selected from the group consisting of $C_{1-22}$ alkyl (meth)acrylates and mixtures thereof; >0 to 50 wt % (preferably, 0.1 to 50 wt %; more preferably, 0.5 to <20 wt %; still more preferably, 1 to 19 wt % most preferably, 4 to 16 wt %), based on weight of the acrylate rich stage, of structural units of a first carbosiloxane monomer of formula (I); 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid acrylate rich stage monomer; and 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated acrylate rich stage monomer having at least two ethylenically unsaturated groups per molecule Preferably, the acrylate rich stage comprises: 63 to 99.9 wt % (preferably, >74 to 98.49 wt %; more preferably, 80.4 to 96.95 wt %; most preferably, 82.17 to 94.68 wt %), based on weight of the acrylate rich stage, of structural units of a monoethylenically unsaturated nonionic acrylate rich stage monomer; wherein the monoethylenically unsaturated nonionic acrylate rich stage monomer is selected from the group consisting of $C_{1-22}$ alkyl (meth)acrylates and mixtures thereof. More preferably, the acrylate rich stage comprises: 63 to 99.9 wt % (preferably, >74 to 98.49 wt %; more preferably, 80.4 to 96.95 wt %; most preferably, 82.17 to 94.68 wt %), based on weight of the acrylate rich stage, of structural units of a monoethylenically unsaturated nonionic acrylate rich stage monomer; wherein the monoethylenically unsaturated nonionic acrylate rich stage monomer is selected from the group consisting of a mixture of at least two $C_{1-8}$ alkyl (meth)acrylates. Still more preferably, the acrylate rich stage comprises: 63 to 99.9 wt % (preferably, >74 to 98.49 wt %; more preferably, 80.4 to 96.95 wt %; most preferably, 82.17 to 94.68 wt %), based on weight of the acrylate rich stage, of structural units of a monoethylenically unsaturated nonionic acrylate rich stage monomer; wherein the monoethylenically unsaturated nonionic acrylate rich stage monomer is selected from the group consisting of a mixture of at least two $C_{1-4}$ alkyl (meth)acrylates. Yet more preferably, the acrylate rich stage comprises: 63 to 99.9 wt % (preferably, >74 to 98.49 wt %; more preferably, 80.4 to 96.95 wt %; most preferably, 82.17 to 94.68 wt %), based on weight of the acrylate rich stage, of structural units of a monoethylenically unsaturated nonionic acrylate rich stage monomer; wherein the monoethylenically unsaturated nonionic acrylate rich stage monomer is selected from the group consisting of a mixture of at least three $C_{1-4}$ alkyl (meth)acrylates. Most preferably, the acrylate rich stage comprises: 63 to 99.9 wt % (preferably, >74 to 98.49 wt %; more preferably, 80.4 to 96.95 wt %; most preferably, 82.17 to 94.68 wt %), based on weight of the acrylate rich stage, of structural units of a monoethylenically unsaturated nonionic acrylate rich stage monomer; wherein the monoethylenically unsaturated nonionic acrylate rich stage monomer is selected from the group consisting of a mixture of at least three $C_{1-4}$ alkyl (meth) acrylates; wherein the mixture includes butyl acrylate, butyl methacrylate and methyl methacrylate.

Preferably, the acrylate rich stage comprises: >0 to 50 wt % (preferably, 0.1 to 50 wt %; more preferably, 0.5 to <20 wt %; still more preferably, 1 to 19 wt % most preferably, 4 to 16 wt %), based on weight of the acrylate rich stage, of a first carbosiloxane monomer of formula (I). More preferably, the acrylate rich stage comprises: >0 to 50 wt % (preferably, 0.1 to 50 wt %; more preferably, 0.5 to <20 wt %; still more preferably, 1 to 19 wt % most preferably, 4 to 16 wt %), based on weight of the acrylate rich stage, of a first carbosiloxane monomer of formula (I), wherein a is 0 to 3 (preferably, 0 to 2; more preferably, 1); wherein d is 0 or 1 (preferably, 0); wherein each $R^1$ is independently selected from the group consisting of a hydrogen, a $C_{1-10}$ alkyl group and an aryl group (preferably, a hydrogen and a $C_{1-10}$ alkyl group; more preferably, a hydrogen and a $C_{1-4}$ alkyl group; still more preferably, a hydrogen and a methyl group; most preferably, a methyl group); wherein each $R^2$ is independently selected from the group consisting of a hydrogen and a $C_{1-10}$ alkyl group (preferably, a hydrogen and a $C_{1-5}$ alkyl group; more preferably, a hydrogen and a $C_{1-4}$ alkyl group; still more preferably, a hydrogen and a methyl group; most preferably, a methyl group); wherein each $R^8$ is a —O—Si$(CH_3)_3$ group; wherein Y is selected from the group consisting of formula (II), (III) and (IV) (preferably, (II) or (III); more preferably, (II)); wherein each $R^4$ and $R^6$ are independently selected from the group consisting of a hydrogen and a methyl group (preferably, a methyl group); wherein each $R^3$ and $R^5$ are independently a $C_{1-10}$ alkylene group (preferably, a $C_{1-7}$ alkylene group; more preferably, a $C_{2-6}$ alkylene group; still more preferably, a $C_{3-5}$ alkylene group; most preferably, a $C_3$ alkylene group (e.g., $—CH_2—CH_2—CH_2—$)); wherein each $R^7$ is independently a $C_{1-10}$ alkyl group; wherein b is 0 to 4 and wherein c is 0 or 1. Most preferably, the acrylate rich stage stage comprises: >0 to 50 wt % (preferably, 0.1 to 50 wt %; more preferably, 0.5 to <20 wt %; still more preferably, 1 to 19 wt % most preferably, 4 to 16 wt %), based on weight of the acrylate rich stage, of structural units of a first carbosiloxane monomer of formula (I), wherein a is 1; wherein d is 0; wherein each $R^1$ is a methyl group; wherein each $R^2$ is a methyl group; wherein Y is of formula (II); wherein each $R^3$ is a $C_{3-5}$ alkylene group; and wherein each $R^4$ is a methyl group.

Preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid acrylate rich stage monomer. More preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid acrylate rich stage monomer; wherein the monoethylenically unsaturated carboxylic acid acrylate rich stage monomer is selected from the group consisting of (meth)acrylic acid, (meth) acryloxypropionic acid, itaconic acid, aconitic acid, maleic acid, maleic anhydride, fumaric acid, crotonic acid, citraconic acid, maleic anhydride, monomethyl maleate, monomethyl fumarate, monomethyl itaconate, other derivatives (such as corresponding anhydride, amides and esters) and mixtures thereof. Still more preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid acrylate rich stage monomer; wherein the monoethylenically unsaturated carboxylic acid acrylate rich stage monomer is selected from the group consisting of acrylic acid, methacrylic acid, itaconic acid, crotonic acid and mixtures thereof. Yet more preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid acrylate rich stage monomer; wherein the monoethylenically unsaturated carboxylic acid acrylate rich stage monomer is selected from the group consisting of at least one of acrylic acid and methacrylic acid. Most preferably, the acrylate rich stage comprises: 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid acrylate rich stage monomer; wherein the monoethylenically unsaturated carboxylic acid acrylate rich stage monomer is methacrylic acid.

Preferably, the acrylate rich stage comprises: 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated acrylate rich stage monomer having at least two ethylenically unsaturated groups per molecule.

More preferably, the acrylate rich stage comprises: 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated acrylate rich stage monomer having at least two ethylenically unsaturated groups per molecule; wherein the multiethylenically unsaturated monomer having at least two ethylenically unsaturated groups per molecule is selected from the group consisting of divinylaromatic compounds, di-(meth)acrylate esters, tri-(meth)acrylate esters, tetra-(methacrylate)esters, di-allyl ethers, tri-allyl ethers, tetra-allyl ethers, di-allyl esters, tri-allyl esters, tetra-allyl esters, allyl (meth)acrylate and mixtures thereof. Still more preferably, the acrylate rich stage comprises: 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated acrylate rich stage monomer having at least two ethylenically unsaturated groups per molecule; wherein the multiethylenically unsaturated monomer having at least two ethylenically unsaturated groups per molecule is selected from the group consisting of divinylbenzene (DVB), trimethylolpropane diallyl ether, tetra-allyl pentaerythritol, triallyl pentaerythritol, diallyl pentaerythritol, dially phthalate, diallyl maleate, triallyl cyanurate, Bisphenol A diallyl ether, allyl sucroses, methylene bisacrylamide, trimethylolpropane triacrylate, allyl methacrylate (ALMA), ethylene glycol dimethacrylate (EGDMA), hexane-1,6-diol diacrylate (HDDA), butylene glycol dimethacrylate (BGDMA) and mixtures thereof. Yet more preferably, the acrylate rich stage comprises: 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated acrylate rich stage monomer having at least two ethylenically unsaturated groups per molecule; wherein the multiethylenically unsaturated monomer having at least two ethylenically unsaturated groups per molecule is selected from the group consisting of DVB, ALMA, EGDMA, HDDA and BGDMA. Yet still more preferably, the acrylate rich stage comprises: 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated acrylate rich stage monomer having at least two ethylenically unsaturated groups per molecule; wherein the multiethylenically unsaturated monomer having at least two ethylenically unsaturated groups per molecule includes ALMA. Most preferably, the acrylate rich stage comprises: 0 to 2 wt % (preferably, 0.01 to 1 wt %; more preferably, 0.05 to 0.1 wt %; most preferably, 0.07 to 0.08 wt %), based on weight of the acrylate rich stage, of structural units of a multiethylenically unsaturated acrylate rich stage monomer having at least two ethylenically unsaturated groups per molecule; wherein the multiethylenically unsaturated monomer having at least two ethylenically unsaturated groups per molecule is ALMA.

Preferably, the multistage polymer of the present invention comprises a carbosiloxane rich stage. More preferably, the multistage polymer of the present invention, comprises: 5 to 40 wt % (preferably, 10 to 35 wt %; more preferably, 15 to 30 wt %; preferably, 18 to 25 wt %), based on weight of the multistage polymer, of a carbosiloxane rich stage. Most preferably, the multistage polymer of the present invention, comprises: 5 to 40 wt % (preferably, 10 to 35 wt %; more preferably, 15 to 30 wt %; preferably, 18 to 25 wt %), based on weight of the multistage polymer, of a carbosiloxane rich stage; wherein the carbosiloxane rich stage comprises: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; and 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a second carbosiloxane monomer of formula (I).

Preferably, the carbosiloxane rich stage comprises: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer. More preferably, the carbosiloxane rich stage comprises: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; wherein the vinyl monomer contains at least one radically polymerizable vinyl group per molecule. Still more preferably, the carbosiloxane rich stage comprises: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; wherein the vinyl monomer is selected from the group consisting of $C_{1-3}$ alkyl acrylates (e.g., methyl acrylate, ethyl acrylate, n-propyl acrylate, isopropyl acrylate); $C_{1-3}$ alkyl methacrylates (e.g., methyl methacrylate, ethyl methacrylate, n-propyl methacrylate, isopropyl methacrylate); monoethylenically unsaturated carboxylic acids (e.g., (meth)acrylic acid, (meth)acryloxypropionic acid, itaconic acid, aconitic acid, maleic acid, maleic anhydride, fumaric acid, crotonic acid, citraconic acid, maleic anhydride, monomethyl maleate, monomethyl fumarate, monomethyl itaconate); $C_{4-20}$ alkyl acrylates (e.g., n-butyl acrylate, isobutyl acrylate, tert-butyl acrylate, n-hexyl acrylate, cyclohexyl acrylate, 2-ethylhexyl acrylate, octyl acrylate, lauryl acrylate, stearyl acrylate); $C_{4-20}$ alkyl methacrylates (e.g., n-butyl methacrylate, isobutyl methacrylate, tert-butyl methacrylate, n-hexyl methacrylate, cyclohexyl methacrylate, 2-ethylhexyl methacrylate, octyl methacrylate, lauryl methacrylate, stearyl methacrylate); aromatic vinyl monomers (e.g., styrene, vinyl toluene, benzyl acrylate, benzyl methacrylate, phenoxyethyl acrylate, phenoxyethyl methacrylate, vinyl pyrrolidone); and mixtures thereof. Yet more preferably, the carbosiloxane rich stage comprises: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; wherein the vinyl monomer is selected from the group consisting of methyl acrylate, ethyl acrylate, n-propyl acrylate, isopropyl acrylate, methyl methacrylate, ethyl methacrylate, n-propyl methacrylate, isopropyl methacrylate, n-butyl acrylate, isobutyl acrylate, tert-butyl acrylate, n-hexyl acrylate, cyclohexyl acrylate, 2-ethylhexyl acrylate, n-butyl methacrylate, isobutyl methacrylate, tert-butyl methacrylate, n-hexyl methacrylate, 2-ethylhexyl methacrylate, methacrylic acid and mixtures thereof. Most preferably, the carbosiloxane rich stage comprises: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; wherein the vinyl monomer includes methyl methacrylate and methacrylic acid.

Preferably Preferably, the carbosiloxane rich stage comprises: 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a second carbosiloxane monomer of formula (I). More preferably, the carbosiloxane rich stage comprises: 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a second carbosiloxane monomer of formula (I), wherein a is 0 to 3 (preferably, 0 to 2; more preferably, 1); wherein d is 0 or 1 (preferably, 0); wherein each $R^1$ is independently selected from the group consisting of a hydrogen, a $C_{1-10}$ alkyl group and an aryl group (preferably, a hydrogen and a $C_{1-10}$ alkyl group; more preferably, a hydrogen and a $C_{1-4}$ alkyl group; still more preferably, a hydrogen and a methyl group; most preferably, a methyl group); wherein each $R^2$ is independently selected from the group consisting of a hydrogen and a $C_{1-10}$ alkyl group (preferably, a hydrogen and a $C_{1-5}$ alkyl group; more preferably, a hydrogen and a $C_{1-4}$ alkyl group; still more preferably, a hydrogen and a methyl group; most preferably, a methyl group); wherein each $R^8$ is a $—O—Si(CH_3)_3$ group; wherein Y is selected from the group consisting of formula (II), (III) and (IV) (preferably, (II) or (III); more preferably, (II)); wherein each $R^4$ and $R^6$ are independently selected from the group consisting of a hydrogen and a methyl group (preferably, a methyl group); wherein each $R^3$ and $R^5$ are independently a $C_{1-10}$ alkylene group (preferably, a $C_{1-7}$ alkylene group; more preferably, a $C_{2-6}$ alkylene group; still more preferably, a $C_{3-5}$ alkylene group; most preferably, a $C_3$ alkylene group (e.g., $—CH_2—CH_2—CH_2—$)); wherein each $R^7$ is independently a $C_{1-10}$ alkyl group; wherein b is 0 to 4 and wherein c is 0 or 1. Most preferably, the carbosiloxane rich stage comprises: 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a second carbosiloxane monomer of formula (I), wherein a is 1; wherein d is 0; wherein each $R^1$ is a methyl group; wherein each $R^2$ is a methyl group; wherein Y is of formula (II); wherein each $R^3$ is a $C_{3-5}$ alkylene group; and wherein each $R^4$ is a methyl group.

Preferably, the aqueous antiperspirant composition of the present invention comprises 0.1 to 35 wt % (preferably, 0.5 to 30 wt %; more preferably, 1 to 25 wt %; most preferably, 1.5 to 20 wt %), based on weight of the aqueous antiperspirant composition, of an antiperspirant aluminum salt. More preferably, the aqueous antiperspirant composition of the present invention comprises 0.1 to 35 wt % (preferably, 0.5 to 30 wt %; more preferably, 1 to 25 wt %; most preferably, 1.5 to 20 wt %), based on weight of the aqueous antiperspirant composition, of an antiperspirant aluminum salt; wherein the an antiperspirant aluminum salt is selected from the group consisting of aluminum halohydrate (e.g., aluminum chlorohydrate), aluminum zirconium halohydrate (e.g., aluminum zirconium chlorohydrate), a complex of zirconium hydroxychloride with an amino acid, a complex of aluminum hydroxychloride with an amino acid and mixtures thereof. Yet more preferably, the aqueous antiperspirant composition of the present invention comprises 0.1 to 35 wt % (preferably, 0.5 to 30 wt %; more preferably, 1 to 25 wt %; most preferably, 1.5 to 20 wt %), based on weight of the aqueous antiperspirant composition, of an antiperspirant aluminum salt; wherein the an antiperspirant aluminum salt is selected from the group consisting of aluminum chlorohydrate, aluminum chlorohydrex, aluminum chlorohydrex polyethylene glycol complex, aluminum chlorohydrex propylene glycol complex, aluminum dichlorohydrate, aluminum dichlorohydrex polyethylene glycol complex, aluminum dichlorohydrex propylene glycol complex, aluminum sesquichloro-hydrate, aluminum sesquichlorohydrex polyethylene glycol complex, aluminum sesquichlorohydrex propylene glycol complex, aluminum sulfate buffered with sodium aluminum lactate, aluminum zirconium octachlorohydrate, aluminum zirconium pentachlorohydrate, aluminum zirconium tetrachlorohydrate, aluminum zirconium trichlorohydrate and mixtures thereof. Sill more preferably, the aqueous antiperspirant composition of the present invention comprises 0.1 to 35 wt % (preferably, 0.5 to 30 wt %; more preferably, 1 to 25 wt %; most preferably, 1.5 to 20 wt %), based on weight of the aqueous antiperspirant composition, of an antiperspirant aluminum salt; wherein the antiperspirant aluminum salt includes aluminum chlorohydrate. Most preferably, the aqueous antiperspirant composition of the present invention comprises 0.1 to 35 wt % (preferably, 0.5 to 30 wt %; more preferably, 1 to 25 wt %; most preferably, 1.5 to 20 wt %), based on weight of the aqueous antiperspirant composition, of an antiperspirant aluminum salt; wherein the antiperspirant aluminum salt is aluminum chlorohydrate.

Preferably, the aqueous antiperspirant composition of the present invention, optionally, further comprises an optional additive. More preferably, the aqueous antiperspirant composition of the present invention, further comprises an optional additive, wherein the optional additive is selected from the group consisting of a fragrances, deodorant active agent, zinc pidolate, emollients, preservatives (e.g., phenoxyethanol), antioxidants, moisturizers, humectants (e.g., glycerin), single stage polymers, rheology modifiers, aesthetic modifiers, Vitamins, skin protectants, oils, emulsifiers (Ceteareth 20), surfactants, pearlizers, opacifiers, consistency factors, thickeners, stabilizers, fats, waxes, bactericides, softeners, lecithins, phospholipids, fillers and mixtures thereof.

Preferably, the aqueous antiperspirant composition of the present invention further comprises a single stage polymer; wherein the single stage polymer and the multistage polymer form a blend; wherein the single stage polymer, comprises 90 to 99.8 wt % (preferably, 95 to 99.5 wt %; more preferably, 97 to 99.25 wt %; most preferably, 98 to 99 wt %), based on solids weight of the single stage polymer, of structural units of a monoethylenically unsaturated nonionic single stage monomer; 0.19 to 10 wt % (preferably, 0.45 to 5 wt %; more preferably, 0.65 to 3 wt %; most preferably, 0.92 to 2 wt %), based on solids weight of the single stage polymer, of structural units of a monoethylenically unsaturated carboxylic acid single stage monomer; and 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %), based on solids weight of the single stage polymer, of structural units of a multiethylenically unsaturated single stage monomer having at least two ethylenically unsaturated groups per molecule.

Preferably, the aqueous antiperspirant composition of the present invention further comprises a single stage polymer; wherein the single stage polymer and the multistage polymer form a blend; wherein the single stage polymer, comprises 90 to 99.8 wt % (preferably, 95 to 99.5 wt %; more preferably, 97 to 99.25 wt %; most preferably, 98 to 99 wt %), based on solids weight of the single stage polymer, of structural units of a monoethylenically unsaturated nonionic single stage monomer; wherein the monoethylenically unsaturated nonionic single stage monomer is selected from the group consisting of a mixture of (i) a $C_{1-5}$ alkyl (meth) acrylate and (ii) a $C_{6-22}$ alkyl (meth)acrylate. More preferably, the aqueous antiperspirant composition of the present invention further comprises a single stage polymer; wherein the single stage polymer and the multistage polymer form a blend; wherein the single stage polymer of the present invention comprises 90 to 99.8 wt % (preferably, 95 to 99.5 wt %; more preferably, 97 to 99.25 wt %; most preferably, 98 to 99 wt %), based on solids weight of the single stage polymer, of structural units of a monoethylenically unsaturated nonionic single stage monomer; wherein the monoethylenically unsaturated nonionic single stage monomer is selected from the group consisting of a mixture of (i) 35 to 75 wt % (preferably, 40 to 70 wt %; more preferably, 50 to 65 wt %; still more preferably, 55 to 62 wt %; yet more preferably, 58 to 61 wt %; most preferably, 59 to 60 wt %), based on weight of structural units of monoethylenically unsaturated nonionic single stage monomer, of a $C_{1-5}$ alkyl (meth)acrylate and (ii) 25 to 65 wt % (preferably, 30 to 60 wt %; more preferably, 35 to 50 wt %; still more preferably, 38 to 45 wt %; yet more preferably, 39 to 42 wt %; most preferably, 40 to 41 wt %), based on weight of structural units of monoethylenically unsaturated nonionic single stage monomer, of a $C_{8-22}$ alkyl (meth)acrylate. Still more preferably, the aqueous antiperspirant composition of the present invention further comprises a single stage polymer; wherein the single stage polymer and the multistage polymer form a blend; wherein the single stage polymer of the present invention comprises 90 to 99.8 wt % (preferably, 95 to 99.5 wt %; more preferably, 97 to 99.25 wt %; most preferably, 98 to 99 wt %), based on solids weight of the single stage polymer, of structural units of a monoethylenically unsaturated nonionic single stage monomer; wherein the monoethylenically unsaturated nonionic single stage monomer is selected from the group consisting of a mixture of (i) 35 to 75 wt % (preferably, 40 to 70 wt %; more preferably, 50 to 65 wt %; still more preferably, 55 to 62 wt %; yet more preferably, 58 to 61 wt %; most preferably, 59 to 60 wt %), based on weight of structural units of monoethylenically unsaturated nonionic single stage monomer, of a $C_{1-4}$ alkyl (meth)acrylate; wherein the $C_{1-4}$ alkyl (meth)acrylate is selected from the group consisting of methyl (meth)acrylate, ethyl (meth)acrylate, n-butyl (meth)acrylate, i-butyl (meth) acrylate, t-butyl (meth)acrylate, mixtures thereof; and (ii) 25 to 65 (preferably, 30 to 60 wt %; more preferably, 35 to 50 wt %; still more preferably, 38 to 45 wt %; yet more preferably, 39 to 42 wt %; most preferably, 40 to 41 wt %), based on weight of structural units of monoethylenically unsaturated nonionic single stage monomer, of a $C_{8-22}$ alkyl (meth)acrylate; wherein the $C_{8-22}$ alkyl (meth)acrylate is selected from the group consisting of cyclo-hexyl (meth) acrylate, 2-ethylhexyl (meth)acrylate, lauryl (meth)acrylate, oleyl (meth)acrylate, palmityl (meth)acrylate, stearyl (meth) acrylate, isodecyl (meth)acrylate, behenyl (meth)acrylate, cetyl-eicosyl (meth)acrylate and mixtures thereof. Most preferably, the aqueous antiperspirant composition of the present invention further comprises a single stage polymer; wherein the single stage polymer and the multistage polymer form a blend; wherein the single stage polymer of the present invention comprises 90 to 99.8 wt % (preferably, 95 to 99.5 wt %; more preferably, 97 to 99.25 wt %; most preferably, 98 to 99 wt %), based on solids weight of the single stage polymer, of structural units of a monoethylenically unsaturated nonionic single stage monomer; wherein the monoethylenically unsaturated nonionic single stage monomer is selected from the group consisting of a mixture of (i) 35 to 75 wt % (preferably, 40 to 70 wt %; more preferably, 50 to 65 wt %; still more preferably, 55 to 62 wt %; yet more preferably, 58 to 61 wt %; most preferably, 59 to 60 wt %), based on solids weight of the single stage polymer, of a $C_{1-4}$ alkyl (meth)acrylate, wherein the $C_{1-4}$ alkyl (meth)acrylate is a mixture of 30 to 40 wt % (preferably, 32 to 36 wt %; more preferably, 33 to 35 wt %; most preferably, 33.9 to 34.5 wt %), based on weight of $C_{1-4}$ alkyl (meth)acrylate, of methyl (meth)acrylate and 60 to 70 wt % (preferably, 64 to 68 wt %; more preferably, 65 to 67 wt %; most preferably, 65.5 to 66.1 wt %), based on weight of $C_{1-4}$ alkyl (meth)acrylate, of n-butyl (meth)acrylate; and (ii) 25 to 65 (preferably, 30 to 60 wt %; more preferably, 35 to 50 wt %; still more preferably, 38 to 45 wt %; yet more preferably, 39 to 42 wt %; most preferably, 40 to 41 wt %), based on solids weight of the single stage polymer, of a $C_{8-22}$ alkyl (meth)acrylate, wherein the $C_{8-22}$ alkyl (meth)acrylate is selected from the group consisting of ethylhexyl (meth) acrylate, lauryl (meth)acrylate, stearyl (meth)acrylate and mixtures thereof (preferably, wherein the $C_{8-22}$ alkyl (meth) acrylate is selected from the group consisting of 2-ethylhexyl acrylate, lauryl methacrylate, stearyl methacrylate and mixtures thereof; more preferably, wherein the $C_{8-22}$ alkyl (meth)acrylate includes 2-ethylhexyl acrylate; most preferably, wherein the $C_{8-22}$ alkyl (meth)acrylate is 2-ethylhexyl acrylate).

Preferably, the aqueous antiperspirant composition of the present invention further comprises a single stage polymer; wherein the single stage polymer and the multistage polymer form a blend; wherein the single stage polymer comprises 0.19 to 10 wt % (preferably, 0.45 to 5 wt %; more preferably, 0.65 to 3 wt %; most preferably, 0.92 to 2 wt %), based on solids weight of the single stage polymer, of structural units of a monoethylenically unsaturated carboxylic acid single stage monomer; wherein the monoethylenically unsaturated carboxylic acid single stage monomer is selected from the group consisting of (meth)acrylic acid, (meth)acryloxypropionic acid, itaconic acid, aconitic acid, maleic acid, maleic anhydride, fumaric acid, crotonic acid, citraconic acid, maleic anhydride, monomethyl maleate, monomethyl fumarate, monomethyl itaconate, and other derivatives such as corresponding anhydride, amides and esters. More preferably, the aqueous antiperspirant composition of the present invention further comprises a single stage polymer; wherein the single stage polymer and the multistage polymer form a blend; wherein the single stage polymer of the present invention comprises 0.19 to 10 wt % (preferably, 0.45 to 5 wt %; more preferably, 0.65 to 3 wt %; most preferably, 0.92 to 2 wt %), based on solids weight of the single stage polymer, of structural units of a monoethylenically unsaturated carboxylic acid single stage monomer; wherein the monoethylenically unsaturated carboxylic acid single stage monomer is selected from the group consisting of acrylic acid, methacrylic acid, itaconic acid, crotonic acid and mixtures thereof. Still more preferably, the aqueous antiperspirant composition of the present invention further comprises a single stage polymer; wherein the single stage polymer and the multistage polymer form a blend; wherein the single stage polymer of the present invention comprises 0.19 to 10 wt % (preferably, 0.45 to 5 wt %; more preferably, 0.65 to 3 wt %; most preferably, 0.92 to 2 wt %), based on solids weight of the single stage polymer, of structural units of a monoethylenically unsaturated carboxylic acid single stage monomer; wherein the monoethylenically unsaturated carboxylic acid single stage monomer is selected from the group consisting of at least one of acrylic acid and methacrylic acid. Most preferably, the aqueous antiperspirant composition of the present invention further comprises a single stage polymer; wherein the single stage polymer and the multistage polymer form a blend; wherein the single stage polymer of the present invention comprises 0.19 to 10 wt % (preferably, 0.45 to 5 wt %; more preferably, 0.65 to 3 wt %; most preferably, 0.92 to 2 wt %), based on solids weight of the single stage polymer, of structural units of a monoethylenically unsaturated carboxylic acid single stage monomer; wherein the monoethylenically unsaturated carboxylic acid single stage monomer is selected from the group consisting of at least one of acrylic acid and methacrylic acid; wherein 75 to 100 mol % (preferably, 85 to 100 mol %; more preferably, 95 to 100 mol %; still more preferably, ≥99 mol %; most preferably, 100 mol %) of the monoethylenically unsaturated carboxylic acid single stage monomer is methacrylic acid.

Preferably, the aqueous antiperspirant composition of the present invention further comprises a single stage polymer; wherein the single stage polymer and the multistage polymer form a blend; wherein the single stage polymer of the present invention comprises 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %), based on solids weight of the single stage polymer, of structural units of a multiethylenically unsaturated single stage monomer having at least two ethylenically unsaturated groups per molecule; wherein the multiethylenically unsaturated single stage monomer having at least two ethylenically unsaturated groups per molecule is selected from the group consisting of divinylaromatic compounds, di-(meth)acrylate esters, tri-(meth)acrylate esters, tetra-(methacrylate)esters, di-allyl ethers, tri-allyl ethers, tetra-allyl ethers, di-allyl esters, tri-allyl esters, tetra-allyl esters, allyl (meth)acrylate and mixtures thereof. More preferably, the aqueous antiperspirant composition of the present invention further comprises a single stage polymer; wherein the single stage polymer and the multistage polymer form a blend; wherein the single stage polymer of the present invention comprises 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %), based on solids weight of the single stage polymer, of structural units of a multiethylenically unsaturated single stage monomer having at least two ethylenically unsaturated groups per molecule; wherein the multiethylenically unsaturated single stage monomer having at least two ethylenically unsaturated groups per molecule is selected from the group consisting of divinylbenzene (DVB), trimethylolpropane diallyl ether, tetra-allyl pentaerythritol, triallyl pentaerythritol, diallyl pentaerythritol, dially phthalate, diallyl maleate, triallyl cyanurate, Bisphenol A diallyl ether, allyl sucroses, methylene bisacrylamide, trimethylolpropane triacrylate, allyl methacrylate (ALMA), ethylene glycol dimethacrylate (EGDMA), hexane-1,6-diol diacrylate (HDDA), butylene glycol dimethacrylate (BGDMA) and mixtures thereof. Still more preferably, the aqueous antiperspirant composition of the present invention further comprises a single stage polymer; wherein the single stage polymer and the multistage polymer form a blend; wherein the single stage polymer of the present invention comprises 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %), based on solids weight of the single stage polymer, of structural units of a multiethylenically unsaturated single stage monomer having at least two ethylenically unsaturated groups per molecule; wherein the multiethylenically unsaturated single stage monomer having at least two ethylenically unsaturated groups per molecule is selected from the group consisting of DVB, ALMA, EGDMA, HDDA and BGDMA. Yet more preferably, the aqueous antiperspirant composition of the present invention further comprises a single stage polymer; wherein the single stage polymer and the multistage polymer form a blend; wherein the single stage polymer of the present invention comprises 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %), based on solids weight of the single stage polymer, of structural units of a multiethylenically unsaturated single stage monomer having at least two ethylenically unsaturated groups per molecule; wherein the multiethylenically unsaturated single stage monomer having at least two ethylenically unsaturated groups per molecule includes ALMA. Most preferably, the aqueous antiperspirant composition of the present invention further comprises a single stage polymer; wherein the single stage polymer and the multistage polymer form a blend; wherein the single stage polymer of the present invention comprises 0.01 to 2 wt % (preferably, 0.02 to 1 wt %; more preferably, 0.03 to 0.5 wt %; still more preferably, 0.05 to 0.1 wt %; most preferably, 0.07 to 0.08 wt %), based on solids weight of the single stage polymer, of structural units of a multiethylenically unsaturated single stage monomer having at least two ethylenically unsaturated groups per molecule; wherein the multiethylenically unsaturated single stage monomer having at least two ethylenically unsaturated groups per molecule is ALMA.

Preferably, the aqueous antiperspirant composition of the present invention further comprises a single stage polymer; wherein the single stage polymer and the multistage polymer form a blend; wherein the blend comprises 25 to 95 wt % (preferably, 30 to 90 wt %; more preferably, 50 to 80 wt %; most preferably, 60 to 70 wt %), based on solids weight of the blend, of the single stage polymer and 5 to 75 wt % (preferably, 10 to 70 wt %; more preferably, 20 to 50 wt %; most preferably, 30 to 40 wt %), based on solids weight of the blend, of a multistage polymer.

Preferably, the aqueous antiperspirant composition of the present invention, optionally, further comprises 0 to 50 wt % (preferably, 1 to 45 wt %; more preferably, 2 to 40 wt %; most preferably, 3 to 35 wt %), based on weight of the aqueous antiperspirant composition, of an oil. More preferably, the aqueous antiperspirant composition of the present invention, optionally further comprises 0 to 50 wt % (preferably, 1 to 45 wt %; more preferably, 2 to 40 wt %; most preferably, 3 to 35 wt %), based on weight of the aqueous antiperspirant composition, of an oil; wherein the oil is selected from the group consisting of synthetic and organic hydrocarbon based oils (e.g., mineral oil; vegetable based oils, such as, esters and triglycerides), silicone based oils and mixtures thereof. Most preferably, the aqueous antiperspirant composition of the present invention, optionally further comprises 0 to 50 wt % (preferably, 1 to 45 wt %; more preferably, 2 to 40 wt %; most preferably, 3 to 35 wt %), based on weight of the aqueous antiperspirant composition, of an oil; wherein the oil is selected from the group consisting of volatile silicone oils, nonvolatile silicone oils, hydrocarbon oils and mixtures thereof.

The term "volatile" as used herein refers to those oils having a measurable vapor pressure at ambient temperature. Volatile silicone oils include, for example, cyclic (cyclomethicone) and linear polydimethylsiloxanes containing from 3 to 9 (preferably, 4 to 5) silicone atoms per molecule. Commercially available volatile silicone oils include DC 200, DC 244, DC 245, DC 344 and DC 345 silicones (available from The Dow Chemical Company); SF-1204, SF-1202 Silicone Fluids, GE 7207 and GE 7158 (available from GE Silicones); and SWS-03314 (available from SWS Silicones Corporation).

Nonvolatile silicone oils include, for example, polyalkyl siloxanes, polyalkylaryl siloxanes and polyether siloxane copolymers. The nonvolatile polyalkyl siloxanes include, for example, polydimethyl siloxanes with viscosities of $5\times10^{-6}$ to 0.1 $m^2/s$ at 25° C. Preferred nonvolatile silicone oils include polydimethyl siloxanes having viscosities of $1\times10^{-5}$ to $4\times10^{-4}$ $m^2/s$ at 25° C. Representative commercial materials include polyalkyl siloxanes, such as, those sold under the Viscasil Series (G.E. Silicones) and the DC 200 series (The Dow Chemical Company); polyalkylaryl siloxanes including polymethylphenyl siloxanes, such as, those sold under the SF 1075 methyl-phenyl fluid (G.E. Silicones) and 556 Cosmetic Grade Fluid (The Dow Chemical Company). Illustrative polyoxyalkylene ether copolymers include SF 1066 (G.E. Silicones) and PEG-10 Dimethicone (Shin-Etsu). Another class of nonvolatile silicones include emulsifying and nonemulsifying silicone elastomers, for example, DowSil 9040 Dimethicone/Vinyl Dimethicone Crosspolymer (The Dow Chemical Company); SFE 839 (G.E. Silicones; and KSG-18 (Shin-Etsu). Silicone wases such as Silwax WS-L (Dimethicone Copolyol Laurate) may also be useful.

Hydrocarbon oils include, for example, mineral oils; fatty alcohols (e.g., cetyl alcohol); esters of $C_{3-8}$ alcohols with $C_{3-8}$ acids (e.g., glyceryl stearate); esters of benzoic acid with $C_{12-18}$ alcohols; $C_{2-6}$ polyols (e.g., glycerol, propylene glycol and sorbitol); polyalkylene glycol polymers and mixtures thereof.

Preferably, the aqueous antiperspirant composition of the present invention, optionally, further comprises 0 to 1 wt % (preferably, 0.005 to 0.8 wt %; more preferably, 0.01 to 0.7 wt %; most preferably, 0.015 to 0.6 wt %), based on weight of the aqueous antiperspirant composition, of a nonionic surfactant. More preferably, the aqueous antiperspirant composition of the present invention, optionally, further comprises 0 to 1 wt % (preferably, 0.005 to 0.8 wt %; more preferably, 0.01 to 0.7 wt %; most preferably, 0.015 to 0.6 wt %), based on weight of the aqueous antiperspirant composition, of a nonionic surfactant; wherein the nonionic surfactant is a nonionic surfactant of formula (VI)

(VI)

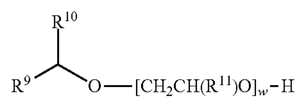

wherein w is an average of 5 to 60 (preferably, 10 to 55; more preferably, 20 to 50, most preferably, 35 to 45); wherein $R^9$ is selected from the group consisting of a hydrogen and a linear or branched $C_{1-20}$ alkyl group; wherein $R^{10}$ is selected from the group consisting of a linear or branched $C_{1-20}$ alkyl group and a linear or branched $C_{1-4}$ hydroxyalkyl group; wherein each $R^{11}$ is independently selected from the group consisting of a hydrogen, a methyl group, an ethyl group, a n-propyl group, an iso-propyl group, a n-butyl group, a 2-butyl group and a 2-methyl-2-butyl group; and with the proviso that sum of the total number of carbon atoms in $R^9$ and $R^{10}$ is 5 to 21. Most preferably, the aqueous antiperspirant composition of the present invention, optionally, further comprises 0 to 1 wt % (preferably, 0.005 to 0.8 wt %; more preferably, 0.01 to 0.7 wt %; most preferably, 0.015 to 0.6 wt %), based on weight of the aqueous antiperspirant composition, of a nonionic surfactant; wherein the nonionic surfactant is a nonionic surfactant of formula (VI); wherein the nonionic surfactant of formula (VI) is of formula (VIa)

(VIa)

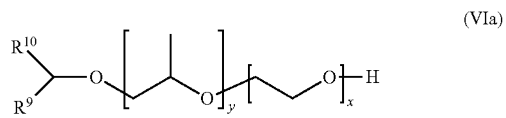

wherein x is an average of 5 to 60 (preferably, 10 to 55; more preferably, 20 to 50, most preferably, 35 to 45); wherein y is an average of 0 to 15 (preferably, 0 to 10; more preferably, 0 to 8, most preferably, 0); wherein $R^9$ is selected from the group consisting of a hydrogen and a linear or branched $C_{1-20}$ alkyl group (preferably, a hydrogen and a linear or branched $C_{1-15}$ alkyl group; more preferably, a linear $C_{1-15}$ alkyl group); wherein $R^{10}$ is selected from the group consisting of a linear or branched $C_{1-20}$ alkyl group and a linear or branched $C_{1-4}$ hydroxyalkyl group (preferably, a linear or branched $C_{1-15}$ alkyl group and a linear or branched $C_{1-4}$ hydroxyalkyl group; more preferably, a linear $C_{1-15}$ alkyl group and a linear or branched $C_{1-3}$ hydroxyalkyl group; most preferably, a linear $C_{1-15}$ alkyl group); and with the proviso that the sum of the total number of carbon atoms in $R^9$ and $R^{10}$ is 5 to 21 (preferably, 6 to 20 carbon atoms; more preferably, 7 to 18 carbon atoms; most preferably, 11 to 15 carbon atoms).

Preferably, the nonionic surfactant has an HLB of >10.

Preferably, the aqueous antiperspirant composition of the present invention, optionally, further comprises an emulsifier. More preferably, the aqueous antiperspirant composition of the present invention, optionally, further comprises an emulsifier, wherein the emulsifier is a silicone polyethers. Still more preferably, the aqueous antiperspirant composition of the present invention, optionally, further comprises an emulsifier, wherein the emulsifier is a silicone polyethers selected from the group consisting of grafted block or block copolymers comprising at least one block of polyorganosiloxane and at least one block of polyether. Polyorganosiloxane blocks may include a polydimethylsiloxane or a poly $C_{2-8}$ alkylmethylsiloxane. Polyether blocks may include a poly(oxy $C_{2-8}$ alkylene)(for example polyoxyethylene and polyoxypropylene). The block copolymers may be linear rake or graft type materials, or ABA type wherein the B is a siloxane polymer group and the A is a poly(oxyalkylene) group. The poly(oxyalkylene) group may comprise polyethylene oxide, polypropylene oxide, or mixed polyethylene oxide/polypropylene oxide groups. Other oxides, such a butylene oxide or phenylene oxide are also possible.

Preferably, the aqueous antiperspirant composition of the present invention, optionally, further comprises a deodorant active agent. More preferably, the aqueous antiperspirant composition of the present invention, optionally further comprises a deodorant active agent, wherein the deodorant active agent is selected from the group consisting of bacteriostatic agents, bactericidal agents (e.g., 2,4,4'-trichloro-2'-hydroxydiphenyl ether (Triclosan); 2,4-dichloro-2'-hydroxydiphenyl ether; 3',4',5'-trichlorosalicylanilide; 1-(3',4'-dichlorophenyl)-3-(4'-chlorophenyl)urea (Triclocarban) and 3,7,11-trimethyldodeca-2,5,10-trienol (Farnesol)); quaternary ammonium salts (e.g., cetyltrimethylammonium salts and cetylpyridinium salts); chlorhexidine and its salts; diglyceryl monocaprate; diglyceryl monolaurate; glyceryl monolaurate; polyhexamethylene biquanide salts; and mixtures thereof. Most preferably, the aqueous antiperspirant composition of the present invention, optionally further comprises a deodorant active agent, wherein the deodorant active agent is selected from the group consisting of 2,4,4'-trichloro-2'-hydroxydiphenyl ether (Triclosan); 2,4-dichloro-2'-hydroxydiphenyl ether; 3',4',5'-trichlorosalicylanilide; 1-(3',4'-dichlorophenyl)-3-(4'-chlorophenyl)urea (Triclocarban); 3,7,11-trimethyldodeca-2,5,10-trienol (Farnesol); cetyltrimethylammonium salts; cetylpyridinium salts; chlorhexidine; chlorhexidine salts; diglyceryl monocaprate; diglyceryl monolaurate; glyceryl monolaurate; polyhexamethylene biquanide salts and mixtures thereof.

Preferably, the aqueous antiperspirant composition of the present invention is an emulsion. More preferably, the aqueous antiperspirant composition of the present invention is an emulsion selected from the group consisting of a water-in-oil emulsion and an oil-in-water emulsion.

Preferably, the aqueous antiperspirant composition of the present invention is a water-in-oil emulsion. More preferably, the aqueous antiperspirant composition of the present invention is a water-in-oil emulsion and further comprises an oil. Still more preferably, the aqueous antiperspirant composition of the present invention is a water-in-oil emulsion and further comprises an oil; wherein the oil is selected from the group consisting of volatile silicone oils, nonvolatile silicone oils, hydrocarbon oils and mixtures thereof. Most preferably, the aqueous antiperspirant composition of the present invention is a water-in-oil emulsion and further comprises an oil; wherein the oil is selected from the group consisting of a mixture of volatile silicone oils, nonvolatile silicone oils and hydrocarbon oils; and wherein the antiperspirant aluminum salt includes an aluminum chlorohydrate.

Preferably, the aqueous antiperspirant composition of the present invention is an oil-in-water emulsion. More preferably, the aqueous antiperspirant compositon of the present invention is an oil-in-water emulsion, further comprising a nonionic surfactant. Most preferably, the aqueous antiperspirant composition of the present invention is an oil-in-water emulsion, further comprising a fragrance and a nonionic surfactant.

Preferably, the aqueous antiperspirant composition of the present invention is an oil-in-water emulsion and further comprises a nonionic surfactant of formula (VI); wherein w is an average of 5 to 60 (preferably, 10 to 55; more preferably, 20 to 50, most preferably, 35 to 45); wherein $R^9$ is selected from the group consisting of a hydrogen and a linear or branched $C_{1-20}$ alkyl group; wherein $R^{10}$ is selected from the group consisting of a linear or branched $C_{1-20}$ alkyl group and a linear or branched $C_{1-4}$ hydroxyalkyl group; wherein each $R^{11}$ is independently selected from the group consisting of a hydrogen, a methyl group, an ethyl group, a n-propyl group, an iso-propyl group, a n-butyl group, a 2-butyl group and a 2-methyl-2-butyl group; and with the proviso that sum of the total number of carbon atoms in $R^9$ and $R^{10}$ is 5 to 21. More preferably, the aqueous antiperspirant composition of the present invention is an oil-in-water emulsion and further comprises a nonionic surfactant of formula (VI); wherein w is an average of 5 to 60 (preferably, 10 to 55; more preferably, 20 to 50, most preferably, 35 to 45); wherein $R^9$ is selected from the group consisting of a hydrogen and a linear or branched $C_{1-20}$ alkyl group; wherein $R^{10}$ is selected from the group consisting of a linear or branched $C_{1-20}$ alkyl group and a linear or branched $C_{1-4}$ hydroxyalkyl group; wherein each $R^{11}$ is independently selected from the group consisting of a hydrogen, a methyl group, an ethyl group, a n-propyl group, an iso-propyl group, a n-butyl group, a 2-butyl group and a 2-methyl-2-butyl group; and with the proviso that sum of the total number of carbon atoms in $R^9$ and $R^{10}$ is 5 to 21; and wherein the antiperspirant aluminum salt includes an aluminum chlorohydrate. Still more preferably, the aqueous antiperspirant composition of the present invention is an oil-in-water emulsion and further comprises a nonionic surfactant of formula (VI); wherein the nonionic surfactant of formula (VI) is of formula (VIa); wherein x is an average of 5 to 60 (preferably, 10 to 55; more preferably, 20 to 50, most preferably, 35 to 45); wherein y is an average of 0 to 15 (preferably, 0 to 10; more preferably, 0 to 8, most preferably, 0); wherein $R^9$ is selected from the group consisting of a hydrogen and a linear or branched $C_{1-20}$ alkyl group (preferably, a hydrogen and a linear or branched $C_{1-15}$ alkyl group; more preferably, a linear $C_{1-15}$ alkyl group); wherein $R^{10}$ is selected from the group consisting of a linear or branched $C_{1-20}$ alkyl group and a linear or branched $C_{1-4}$ hydroxyalkyl group (preferably, a linear or branched $C_{1-15}$ alkyl group and a linear or branched $C_{1-4}$ hydroxyalkyl group; more preferably, a linear $C_{1-15}$ alkyl group and a linear or branched $C_{1-3}$ hydroxyalkyl group; most preferably, a linear $C_{1-15}$ alkyl group); with the proviso that the sum of the total number of carbon atoms in $R^9$ and $R^{10}$ is 5 to 21 (preferably, 6 to 20 carbon atoms; more preferably, 7 to 18 carbon atoms; most preferably, 11 to 15 carbon atoms); and wherein the antiperspirant aluminum salt includes an aluminum chlorohydrate. Most preferably, the aqueous antiperspirant composition of the present invention is an oil-in-water emulsion and further comprises a nonionic surfactant of formula (VI); wherein the nonionic surfactant of formula (VI) is of formula (VIa); wherein xis an average of 35 to 45; wherein y is 0; wherein $R^9$ is a linear $C_{1-15}$ alkyl group; wherein $R^{10}$ is a linear $C_{1-15}$ alkyl group; with the proviso that the sum of the total number of carbon atoms in $R^9$ and $R^{10}$ is 11 to 15 carbon atoms; and wherein the antiperspirant aluminum salt includes an aluminum chlorohydrate.

Preferably, the method of inhibiting perspiration of the present invention, comprises: providing water; providing an antiperspirant aluminum salt; selecting a sweat repellent polymer, wherein the sweat repellent polymer is selected to have a sweat contact angle of ≥30° (preferably, ≥35°; more preferably, ≥40°; still more preferably, ≥45°; most preferably, ≥50°) and wherein the sweat repellent polymer is a multistage polymer comprising: (a) an acrylate rich stage (preferably, 60 to 95 wt %; more preferably, 65 to 90 wt %; still more preferably, 70 to 85 wt %; most preferably, 75 to 82 wt %), based on weight of the multistage polymer, of the acrylate rich stage); wherein the acrylate rich stage comprises: 38 to <100 wt % (preferably, 44 to 99.39 wt %; more preferably, >77 to 98.73 wt %; still more preferably, 78.9 to 97.95 wt %; most preferably, 82.17 to 94.68 wt %), based on weight of the acrylate rich stage, of structural units of a monoethylenically unsaturated nonionic acrylate rich stage monomer, wherein the monoethylenically unsaturated nonionic acrylate rich stage monomer is selected from the group consisting of $C_{1-22}$ alkyl (meth)acrylates and mixtures thereof; >0 to 50 wt % (preferably, 0.1 to 50 wt %; more preferably, 0.5 to <20 wt %; still more preferably, 1 to 19 wt % most preferably, 4 to 16 wt %), based on weight of the acrylate rich stage, of structural units of a first carbosiloxane monomer of formula (I); wherein a is 0 to 3 (preferably, 0 to 2; most preferably, 1); wherein d is 0 or 1 (preferably, 0);

wherein each $R^1$ is independently selected from the group consisting of a hydrogen, a $C_{1-10}$ alkyl group and an aryl group (preferably, a hydrogen and a $C_{1-10}$ alkyl group; more preferably, a hydrogen and a $C_{1-4}$ alkyl group; still more preferably, a hydrogen and a methyl group; most preferably, a methyl group); wherein each $R^2$ is independently selected from the group consisting of a hydrogen and a $C_{1-10}$ alkyl group (preferably, a hydrogen and a $C_{1-5}$ alkyl group; more preferably, a hydrogen and a $C_{1-4}$ alkyl group; still more preferably, a hydrogen and a methyl group; most preferably, a methyl group); wherein each $R^8$ is a —O—Si$(CH_3)_3$ group; wherein Y is selected from the group consisting of formula (II), (III) and (IV) (preferably, (II) or (III); most preferably, (II)); wherein each $R^4$ and $R^6$ are independently selected from the group consisting of a hydrogen and a methyl group (preferably, a methyl group); wherein each $R^3$ and $R^5$ are independently a $C_{1-10}$ alkylene group (preferably, a $C_{1-7}$ alkylene group; more preferably, a $C_{2-6}$ alkylene group; still more preferably, a $C_{3-5}$ alkylene group; most preferably, a $C_3$ alkylene group (e.g., —$CH_2$—$CH_2$—$CH_2$—)); wherein each $R^7$ is independently a $C_{1-10}$ alkyl group; wherein b is 0 to 4; wherein c is 0 or 1; 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid acrylate rich stage monomer; and 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated acrylate rich stage monomer having at least two ethylenically unsaturated groups per molecule; and (b) a carbosiloxane rich stage (preferably, 5 to 40 wt % (more preferably, 10 to 35 wt %; still more preferably, 15 to 30 wt %; most preferably, 18 to 25 wt %), based on weight of the multistage polymer, of the carbosiloxane rich stage), comprising: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; and 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a second carbosiloxane monomer of formula (I); wherein the first carbosiloxane monomer of formula (I) and the second carbosiloxane monomer of formula (I) are the same or different (preferably, wherein the first carbosiloxane monomer of formula (I) and the second carbosiloxane monomer of formula (I) are the same)(preferably, wherein the multistage polymer is an emulsion polymer)(more preferably, wherein the multistage polymer is an emulsion polymer, comprising an acrylate rich stage as a first stage and a carbosiloxane rich stage as a second stage); providing the selected sweat repellent polymer; combining the water, the antiperspirant aluminum salt and the selected sweat repellent polymer to form an aqueous antiperspirant composition; wherein the aqueous antiperspirant composition is an emulsion; and applying the aqueous antiperspirant composition on skin (preferably, skin of the underarm region) to form a film (preferably, wherein the sweat repellent polymer is an emulsion polymer).

More preferably, the method of inhibiting perspiration of the present invention, comprises: providing water; providing an antiperspirant aluminum salt; providing a fragrance; selecting a sweat repellent polymer, wherein the sweat repellent polymer is selected to have a sweat contact angle of ≥30° (preferably, ≥35°; more preferably, ≥40°; still more preferably, ≥45°; most preferably, ≥50°) and wherein the sweat repellent polymer is a multistage polymer comprising: (a) an acrylate rich stage (preferably, 60 to 95 wt %; more preferably, 65 to 90 wt %; still more preferably, 70 to 85 wt %; most preferably, 75 to 82 wt %), based on weight of the multistage polymer, of the acrylate rich stage); wherein the acrylate rich stage comprises: 38 to <100 wt % (preferably, 44 to 99.39 wt %; more preferably, >77 to 98.73 wt %; still more preferably, 78.9 to 97.95 wt %; most preferably, 82.17 to 94.68 wt %), based on weight of the acrylate rich stage, of structural units of a monoethylenically unsaturated nonionic acrylate rich stage monomer, wherein the monoethylenically unsaturated nonionic acrylate rich stage monomer is selected from the group consisting of $C_{1-22}$ alkyl (meth) acrylates and mixtures thereof; >0 to 50 wt % (preferably, 0.1 to 50 wt %; more preferably, 0.5 to <20 wt %; still more preferably, 1 to 19 wt % most preferably, 4 to 16 wt %), based on weight of the acrylate rich stage, of structural units of a first carbosiloxane monomer of formula (I); wherein a is 0 to 3 (preferably, 0 to 2; most preferably, 1); wherein d is 0 or 1 (preferably, 0); wherein each $R^1$ is independently selected from the group consisting of a hydrogen, a $C_{1-10}$ alkyl group and an aryl group (preferably, a hydrogen and a $C_{1-10}$ alkyl group; more preferably, a hydrogen and a $C_{1-4}$ alkyl group; still more preferably, a hydrogen and a methyl group; most preferably, a methyl group); wherein each $R^2$ is independently selected from the group consisting of a hydrogen and a $C_{1-10}$ alkyl group (preferably, a hydrogen and a $C_{1-5}$ alkyl group; more preferably, a hydrogen and a $C_{1-4}$ alkyl group; still more preferably, a hydrogen and a methyl group; most preferably, a methyl group); wherein each $R^8$ is a —O—Si$(CH_3)_3$ group; wherein Y is selected from the group consisting of formula (II), (III) and (IV) (preferably, (II) or (III); most preferably, (II)); wherein each $R^4$ and $R^6$ are independently selected from the group consisting of a hydrogen and a methyl group (preferably, a methyl group); wherein each $R^3$ and $R^5$ are independently a $C_{1-10}$ alkylene group (preferably, a $C_{1-7}$ alkylene group; more preferably, a $C_{2-6}$ alkylene group; still more preferably, a $C_{3-5}$ alkylene group; most preferably, a $C_3$ alkylene group (e.g., —$CH_2$—$CH_2$—$CH_2$—)); wherein each $R^7$ is independently a $C_{1-10}$ alkyl group; wherein b is 0 to 4; wherein c is 0 or 1; 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid acrylate rich stage monomer; and 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated acrylate rich stage monomer having at least two ethylenically unsaturated groups per molecule; and (b) a carbosiloxane rich stage (preferably, 5 to 40 wt % (more preferably, 10 to 35 wt %; still more preferably, 15 to 30 wt %; most preferably, 18 to 25 wt %), based on weight of the multistage polymer, of the carbosiloxane rich stage), comprising: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; and 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a second carbosiloxane monomer of formula (I); wherein the first carbosiloxane monomer of formula (I) and the second carbosiloxane monomer of formula (I) are the same or different (preferably, wherein the first carbosiloxane monomer of formula (I) and the second carbosiloxane monomer of formula (I) are the same)(preferably, wherein the multistage polymer is an emulsion polymer)(more preferably, wherein the multistage polymer is an emulsion polymer, comprising an acrylate rich stage as a first stage and a carbosiloxane rich stage as a second stage); providing the selected sweat repellent polymer; providing a nonionic surfactant of formula (VI); wherein w is an average of 5 to 60 (preferably, 10 to 55; more preferably, 20 to 50, most preferably, 35 to 45); wherein $R^9$ is selected from the group consisting of a hydrogen and a linear or branched $C_{1-20}$ alkyl group; wherein $R^{10}$ is selected from the group consisting of a linear or branched $C_{1-20}$ alkyl group and a linear or branched $C_{1-4}$ hydroxyalkyl group; wherein each $R^{11}$ is independently selected from the group consisting of a hydrogen, a methyl group, an ethyl group, a n-propyl group, an iso-propyl group, a n-butyl group, a 2-butyl group and a 2-methyl-2-butyl group; and with the proviso that sum of the total number of carbon atoms in $R^9$ and $R^{10}$ is 5 to 21; combining the water, the antiperspirant aluminum salt, the fragrance, the selected sweat repellent polymer and the nonionic surfactant to form an aqueous antiperspirant composition; wherein the aqueous antiperspirant composition is an oil-in-water emulsion; and applying the aqueous antiperspirant composition on skin (preferably, skin of the underarm region) to form a film; wherein fragrance is released when the film is exposed to perspiration (preferably, wherein the sweat repellent polymer is an emulsion polymer).

More preferably, the method of inhibiting perspiration of the present invention, comprises: providing water; providing an antiperspirant aluminum salt; providing a fragrance; selecting a sweat repellent polymer, wherein the sweat repellent polymer is selected to have a sweat contact angle of ≥30° and wherein the sweat repellent polymer is a multistage polymer comprising: (a) an acrylate rich stage (preferably, 60 to 95 wt %; more preferably, 65 to 90 wt %; still more preferably, 70 to 85 wt %; most preferably, 75 to 82 wt %), based on weight of the multistage polymer, of the acrylate rich stage); wherein the acrylate rich stage comprises: 38 to <100 wt % (preferably, 44 to 99.39 wt %; more preferably, >77 to 98.73 wt %; still more preferably, 78.9 to 97.95 wt %; most preferably, 82.17 to 94.68 wt %), based on weight of the acrylate rich stage, of structural units of a monoethylenically unsaturated nonionic acrylate rich stage monomer, wherein the monoethylenically unsaturated nonionic acrylate rich stage monomer is selected from the group consisting of $C_{1-22}$ alkyl (meth)acrylates and mixtures thereof; >0 to 50 wt % (preferably, 0.1 to 50 wt %; more preferably, 0.5 to <20 wt %; still more preferably, 1 to 19 wt % most preferably, 4 to 16 wt %), based on weight of the acrylate rich stage, of structural units of a first carbosiloxane monomer of formula (I); wherein a is 0 to 3 (preferably, 0 to 2; most preferably, 1); wherein d is 0 or 1 (preferably, 0); wherein each $R^1$ is independently selected from the group consisting of a hydrogen, a $C_{1-10}$ alkyl group and an aryl group (preferably, a hydrogen and a $C_{1-10}$ alkyl group; more preferably, a hydrogen and a $C_{1-4}$ alkyl group; still more preferably, a hydrogen and a methyl group; most preferably, a methyl group); wherein each $R^2$ is independently selected from the group consisting of a hydrogen and a $C_{1-10}$ alkyl group (preferably, a hydrogen and a $C_{1-5}$ alkyl group; more preferably, a hydrogen and a $C_{1-4}$ alkyl group; still more preferably, a hydrogen and a methyl group; most preferably, a methyl group); wherein each $R^8$ is a $—O—Si(CH_3)_3$ group; wherein Y is selected from the group consisting of formula (II), (III) and (IV) (preferably, (II) or (III); most preferably, (II)); wherein each $R^4$ and $R^6$ are independently selected from the group consisting of a hydrogen and a methyl group (preferably, a methyl group); wherein each $R^3$ and $R^5$ are independently a $C_{1-10}$ alkylene group (preferably, a $C_{1-7}$ alkylene group; more preferably, a $C_{2-6}$ alkylene group; still more preferably, a $C_{3-5}$ alkylene group; most preferably, a $C_3$ alkylene group (e.g., $—CH_2—CH_2—CH_2—$)); wherein each $R^7$ is independently a $C_{1-10}$ alkyl group; wherein b is 0 to 4; wherein c is 0 or 1; 0 to 10 wt % (preferably, 0.5 to 5 wt %; more preferably, 0.75 to 2.5 wt %; still more preferably, 1 to 2 wt %; most preferably, 1.25 to 1.75 wt %), based on weight of the acrylate rich stage, of structural units of a monoethylenically unsaturated carboxylic acid acrylate rich stage monomer; and 0 to 2 wt % (preferably, 0.01 to 1 wt %; more preferably, 0.02 to 0.5 wt %; still more preferably, 0.05 to 0.1 wt %; most preferably, 0.07 to 0.08 wt %), based on weight of the acrylate rich stage, of structural units of a multiethylenically unsaturated acrylate rich stage monomer having at least two ethylenically unsaturated groups per molecule; and (b) a carbosiloxane rich stage (preferably, 5 to 40 wt % (more preferably, 10 to 35 wt %; still more preferably, 15 to 30 wt %; most preferably, 18 to 25 wt %), based on weight of the multistage polymer, of the carbosiloxane rich stage), comprising: 0 to 90 wt % (preferably, 10 to <50 wt %; more preferably, 12.5 to 30 wt %; still more preferably, 15 to 25 wt %; most preferably, 19 to 21 wt %), based on weight of the carbosiloxane rich stage, of structural units of a vinyl monomer; and 10 to 100 wt % (preferably, >50 to 90 wt %; more preferably, 70 to 87.5 wt %; still more preferably, 75 to 85 wt %; most preferably, 79 to 81 wt %), based on weight of the carbosiloxane rich stage, of structural units of a second carbosiloxane monomer of formula (I); wherein the first carbosiloxane monomer of formula (I) and the second carbosiloxane monomer of formula (I) are the same or different (preferably, wherein the first carbosiloxane monomer of formula (I) and the second carbosiloxane monomer of formula (I) are the same)(preferably, wherein the multistage polymer is an emulsion polymer)(more preferably, wherein the multistage polymer is an emulsion polymer, comprising an acrylate rich stage as a first stage and a carbosiloxane rich stage as a second stage); providing the selected sweat repellent polymer; providing a nonionic surfactant of formula (VI); wherein the nonionic surfactant of formula (VI) provided is of formula (VIa); wherein x is an average of 35 to 45; wherein y is 0; wherein $R^9$ is a linear $C_{1-15}$ alkyl group; wherein $R^{10}$ is selected a linear $C_{1-15}$ alkyl group; and with the proviso that the sum of the total number of carbon atoms in $R^9$ and $R^{10}$ is 11 to 15; combining the water, the antiperspirant aluminum salt, the fragrance, the selected sweat repellent polymer and the nonionic surfactant to form an aqueous antiperspirant composition; wherein the aqueous antiperspirant composition is an oil-in-water emulsion; and applying the aqueous antiperspirant composition on skin (preferably, skin of the underarm region) to form a film; wherein fragrance is released when the film is exposed to perspiration (preferably, wherein the sweat repellent polymer is an emulsion polymer).

Preferably, the sweat repellent polymer is selected to have a sweat contact angle of ≥30° (preferably, ≥35°; more preferably, ≥40°; still more preferably, ≥45°; most preferably, ≥50°); wherein the sweat contact angle is determined using a test formulation comprising: 12 wt %, based on weight of the test formulation, of a 2 cSt polydimethylsiloxane fluid; 2 wt %, based on weight of the test formulation, of lauryl PEG-10 tris(trimethylsiloxy)silylethyl dimethicone; 4 wt %, based on weight of the test formulation, of phenyl trimethicone; 5 wt %, based on weight of the test formulation, of aluminum chlorohydrate; 5 wt %, based on weight of the test formulation, of glycerin; 12.5 wt %, based on weight of the test formulation, propylene glycol; 0.5 wt %, based on weight of the test formulation, phenoxyethanol (and) ethylhexylglycerin; 2 wt %, based on weight of the test formulation, of solids of the sweat repellent polymer; and the remainer of the test formulation being deionized water; wherein the sweat contact angle for the sweat repellent polymer is measured by drawing down a layer of the test formulation on a plastic substrate using a doctor blade with a 3 mil gap to form a deposited layer; allowing the deposited layer to air dry for 24 hours at 72° F. and 50% relative humidity to form an air dried layer; then placing a drop of a pH adjusted artificial sweat solution on the air dried layer and measuring the contact angle at 200 seconds after placement of the drop using a drop shape analyzer (e.g., Kruss DSA 100 drop shape analyzer); wherein the pH adjusted artificial sweat composition is prepared from an artificial sweat composition comprising: 0.025 wt %, based on weight of the artificial sweat composition, of sodium bicarbonate; 0.046 wt %, based on weight of the artificial sweat composition, of potassium chloride; 0.160 wt %, based on weight of the artificial sweat composition, of sodium chloride; 0.150 wt %, based on weight of the artificial sweat composition, of an 85 wt % aqueous lactic acid solution; 0.015 wt %, based on weight of the artificial sweat composition, of a 20 wt % aqueous glucose solution; 0.06 wt %, based on weight of the artificial sweat composition, urea; 0.062 wt %, based on weight of the artificial sweat composition, of a 29 wt % aqueous ammonia solution; and the remainder of the artificial sweat composition being deionized water; and wherein the artificial sweat composition is adjusted to a pH of 5.3 using a 5 wt % aqueous sodium hydroxide solution to form the pH adjusted artificial sweat composition (preferably, wherein the sweat repellent polymer is an emulsion polymer).

Some embodiments of the present invention will now be described in detail in the following Examples.

The monomer abbreviations used in the Examples are described in TABLE 1.

TABLE 1

| Abbreviation | Monomer |
| --- | --- |
| BA | Butyl Acrylate |
| BMA | Butyl Methacrylate |
| MMA | Methyl Methacrylate |
| MAA | Methacrylic Acid |
| ALMA | Allyl Methacrylate |
| MD'M-ALMA | 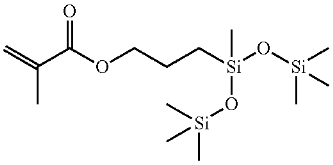 [SMILES: C=C(C)C(=O)OCCC[Si](C)(O[Si](C)(C)C)O[Si](C)(C)C] |

Example S1: Multistage Polymer

A 2-liter round-bottom flask equipped with an overhead stirrer, thermocouple, condenser and inlets for the addition of monomer and initiators was charged with deionized water (262.2 g), a 50% aqueous cyclodextrin solution (15.2 g; CAVASOL™ W7 MTL from Wacker Fine Chemicals), a 31.5% aqueous Aerosol™ A102 surfactant solution (20.5 g; from Solvay) and sodium carbonate (3.4 g). The flask contents were then stirred and heated at 85° C. A first monomer emulsion was prepared by charging deionized water (294.9 g) and 31.5% aqueous Aerosol™ A102 surfactant solution (8.7 g) to a first container and set to stir. After the surfactant was incorporated into the water, butyl acrylate (BA)(121.6 g), butyl methacrylate (BMA)(264.5 g), carbosiloxane monomer (MD'M-ALMA)(60.8 g); methyl methacrylate (MMA)(152.0 g), methacrylic acid (MAA)(9.1 g) and allyl methacrylate (ALMA)(0.5 g) were added slowly to the stirring mixture in the first container. A second monomer emulsion was prepared by charging deionized water (76.0 g) and 31.5% aqueous Aerosol™ A102 surfactant solution (2.2 g) to a second container and set to stir. After the surfactant was incorporated into the water, carbosiloxane monomer (MD'M-ALMA)(121.6 g), methyl methacrylate (MMA)(28.1 g) and methacrylic acid (MAA) (2.3 g) was added slowly to the stirring mixture in the second container. A cofeed catalyst solution was also prepared by charging sodium persulfate (1.5 g) and deionized water (40.3) in another container. A cofeed buffer solution was prepared by charging sodium carbonate (1.5 g) and deionized water (40.3 g) in another container. When the flask contents reached a temperature of 85° C., 34.2 g of the first monomer emulsion was charged to the flask, followed with a deionized water rinse (15.2 g), followed by an initiator solution of sodium persulfate (3.4 g) in deionized water (15.2 g). After initial polymerization and at 85° C., a cofeed to the flask contents of the first monomer emulsion was begun at a rate of 6.5 g per minute for 15 minutes and 13.01 g per minute for 60 minutes thereafter. Simultaneously, the catalyst and buffer cofeeds were begun at a rate of 0.44 g per minute for 95 minutes. After the first monomer emulsion was finished transferring to the flask contents, the second monomer emulsion was introduced to the flask contents at a rate of 11.51 g per minute for 20 minutes. The second monomer emulasion was feed to the flask contents through a Centrifuge Force In-Line mixer/homogenizer set at 7,000 rpm to emulsify the second monomer emulsion. At completion of the second monomer emulsion feed and catalyst/buffer cofeed, the flask contents were chased to reduce the amount of residual monomers. The multistage polymer composition obtained is provided in TABLE 2.

TABLE 2

| Multistage polymer of Example S1 | | | | | | | | | | |
|---|---|---|---|---|---|---|---|---|---|---|
| Acrylate rich stage | | | | | | | Carbosiloxane rich stage | | | |
| | Monomer (wt %) | | | | | | | Monomer (wt %) | | |
| wt % | BA | BMA | MMA | MAA | MD'M-ALMA | ALMA (wt %) | wt % | MAA | MMA | MD'M-ALMA |
| 80 | 20.0 | 43.5 | 25.0 | 1.5 | 10.0 | 0.075 | 20 | 1.5 | 18.5 | 80.0 |

Comparative Example C1 and Example 1: Aqueous Antiperspirant Compositions

Water-in-oil emulsion aqueous antiperspirant compositions were prepared having formulations according to Comparative Example C1 and Example 1 as noted in TABLE 3.

TABLE 3

| Ingredient | Aqueous Antiperspirant C1 (wt %) | 1 (wt %) |
|---|---|---|
| Dimethicone[1] | 12.0 | 12.0 |
| Lauryl PEG-10 tris(trimethylsiloxy)silylethyl Dimethicone[2] | 2.00 | 2.00 |
| Phenyl trimethicone[3] | 4.00 | 4.00 |
| Aluminum chlorohydrate | 5.00 | 5.00 |
| Glycerin | 5.00 | 5.00 |
| Propylene glycol | 12.50 | 12.50 |
| Phenoxyethanol (and) ethylhexylglycerin | 0.50 | 0.50 |
| Multistage polymer of Example S1 | — | 2.00 |
| Deionized water | q.s. 100 | |

[1]PMX 200 fluid available from Dow Silicones Corporation
[2]DowSil ™ 5300 available from Dow Silicones Corporation
[3]DowSil ™ 556 available from Dow Silicones Corporation

Sweat Repellency

The sweat repellency of the water-in-oil emulsion roll-on antiperspirant compositions of Comparative Example C1 and Example 1 were evaluated by measuring the contact angle of artificial sweat on the surface of a film drawndown therefrom. For each roll-on antiperspirant composition a film was coated on a LENETA black plastic chart by drawdown using a doctor blade with a 3 mil gap to form a deposited layer. The samples were allowed to air dry in a controlled environment (72° F., 50% relative humidity) for a minimum of 24 hours. The sweat repellency was determined by placing droplets of an artificial sweat having the composition noted in TABLE 4 and taking sweat contact angle measurements at 4 seconds (expressed as t=0 s) and at 200 seconds (expressed as t=200 s) using a drop shape analyzer (Kruss DSA 100). Each sample was characterized using 5 separate drops of artificial sweat. The average sweat contact angle measurements obtained for each sample at t=0 s and t=200 s are provided in Table 5.

TABLE 4

| Ingredient | wt % |
|---|---|
| Sodium bicarbonate | 0.025 |
| Potassium chloride | 0.046 |
| Sodium chloride | 0.160 |
| Aqueous lactic acid solution (85 wt %) | 0.150 |

TABLE 4-continued

| Ingredient | wt % |
|---|---|
| Aqueous glucose solution (20 wt %) | 0.015 |
| Urea | 0.060 |
| Aqueous ammonia solution (29 wt %) | 0.062 |
| Deionized water | q.s. 100 |
| Aqueous sodium hydroxide solution (5 wt %) | adjusted to pH of 5.3 |

TABLE 5

| Example | Contact angle (in °) t = 0 s | t = 200 s |
|---|---|---|
| C1 | 27.8 | 23.6 |
| 1 | 62.5 | 52.2 |

Fragrance Mixture

A fragrance mixture was prepared having the composition noted in TABLE 6.

TABLE 6

| Ingredient | (wt %) |
|---|---|
| Phenyl ether acetate | 16.7 |
| D-limonene | 16.7 |
| Octanal | 16.7 |
| Linalool | 16.7 |
| Citral | 16.6 |
| Geraniol | 16.6 |

Comparative Example C2 and Example 2: Aqueous Antiperspirant Compositions

Oil-in-water emulsion aqueous antiperspirant compositions were prepared having formulations according to Comparative Example C2 and Example 2 as noted in TABLE 7.

TABLE 7

| Ingredient | Aqueous Antiperspirant C2 (wt %) | 2 (wt %) |
|---|---|---|
| Aqueous aluminum chlorohydrate solution (50 wt %) | 30.00 | 30.00 |
| Ceteareth 20 | 3.00 | 3.00 |
| Cetyl alcohol | 2.00 | 2.00 |
| Glyceryl stearate | 1.50 | 1.50 |

TABLE 7-continued

| Ingredient | Aqueous Antiperspirant C2 (wt %) | 2 (wt %) |
|---|---|---|
| Fragrance mixture according to TABLE 6 | 1.00 | 1.00 |
| Nonionic surfactant[1] | 0.18 | 0.12 |
| Multistage polymer of Example S1 | — | 2.00 |
| Deionized water | q.s. 100 | |

[1]Tergitol™ 15-S-40 (70 wt % solids) available from The Dow Chemical Company

Fragrance Retention

The fragrance retention of the oil-in-water emulsion aqueous antiperspirant compositions of Comparative Example C2 and Example 2 was tested. A 20 μL sample of each composition was added to a separate 22 mL headspace vial, dried in a controlled environment (72° F., 50% relative humidity) for 6 hours and then the vials were capped with a crimper. Three replicates were prepared for each composition. The samples were then analyzed with headspace GC/MS. The GC conditions used are provided in TABLE 8. Quantification was performed using external calibration standards covering the range of 10-1,000 ppmv. The normalized fragrance compound concentration (ppmv/g of original fragrance compound) detected by headspace GC after exposure to air for 6 hours are provided in TABLE 9.

TABLE 8

| | |
|---|---|
| Instrument | Agilent 7890 GC coupled with an Agilent 5977 MSD and 7697A headspace sampler |
| Column | Agilent DB-WaxUI, 30 m × 0.25 mm × 0.25 μm film |
| GC Oven | Initial 50° C. (hold 2 minutes) to 250° C. at 20° C./minute (hold 8 minutes) Total run time: 20 minutes |
| Carrier gas | Helium at constant flow of 1.4 mL/min |
| Inlet | Split ratio: 10:1 |
| | Temperature: 240° C. |
| MS | Transfer line temperature: 250° C. |
| Detector | MS Ion source (EI) temperature: 230° C. |
| | MS Quad temperature: 150° C. |
| | EM Volts: 2312 V |
| | Energy: 70 eV |
| | Emission: 35 μA |
| | Gain factor: 0.5 |
| | SIM ions: m/z 68, 69, 71, 84, 91, 104; 50 ms dwell time for each ion |
| Headspace | Oven temperature: 50° C. |
| conditions | Incubation time: 10 min |
| | Loop temperature: 60° C. |
| | Transfer line temperature: 170° C. |
| | Loop size: 1 mL |
| | Vial equilibration time: 10 min |
| | Injection duration: 0.2 mL |

TABLE 9

| Fragrance compound | Example # Normalized fragrance concentration in headspace after 6 hrs C2 (ppmv/g) | 2 (ppmv/g) |
|---|---|---|
| Phenyl ethyl acetate | 161 | 347 |
| D-Limonene | 101 | 1,220 |
| Octanal | 76 | 225 |
| Linalool | 95 | 222 |
| Citral | 260 | 483 |
| Geraniol | 452 | 445 |

We claim:

1. An aqueous antiperspirant composition, comprising:

(A) water;

(B) a sweat repellent polymer, wherein the sweat repellent polymer comprises a multistage polymer comprising:

(a) an acrylate rich stage comprising:

38 to <100 wt %, based on weight of the acrylate rich stage, of structural units of a monoethylenically unsaturated nonionic acrylate rich stage monomer, wherein the monoethylenically unsaturated nonionic acrylate rich stage monomer is selected from the group consisting of $C_{1-22}$ alkyl (meth)acrylates and mixtures thereof;

>0 to 50 wt %, based on weight of the acrylate rich stage, of structural units of a first carbosiloxane monomer of formula (I)

(I)

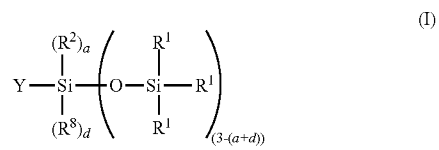

wherein a is 1; wherein d is 0; wherein each $R^1$ is independently selected from the group consisting of a hydrogen, a $C_{1-10}$ alkyl group and an aryl group; wherein each $R^2$ is independently selected from the group consisting of a hydrogen and a $C_{1-10}$ alkyl group; wherein each $R^8$ is a —O—Si$(CH_3)_3$ group; wherein Y is selected from the group consisting of formulas (II), (III) and (IV)

(II)

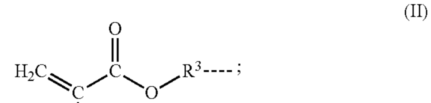

(III)

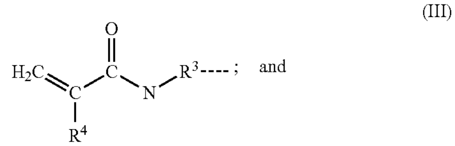

and (IV)

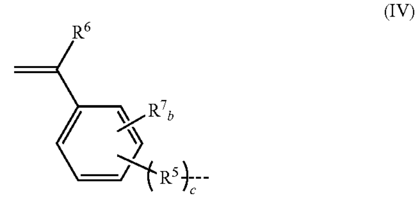

wherein each $R^4$ and $R^6$ are independently selected from the group consisting of a hydrogen and a methyl group; wherein each $R^3$ and $R^5$ are independently a $C_{1-10}$ alkylene group; wherein each $R^7$ is independently a $C_{1-10}$ alkyl group; wherein b is 0 to 4; wherein c is 0 or 1;

0 to 10 wt %, based on weight of the acrylate rich stage, of structural units of a monoethylenically unsaturated carboxylic acid acrylate rich stage monomer; and 0 to 2 wt %, based on weight of the acrylate rich stage, of structural units of a multiethylenically unsaturated acrylate rich stage monomer having at least two ethylenically unsaturated groups per molecule; and (b) a carbosiloxane rich stage, comprising:

0 to 90 wt %, based on weight of the carbosiloxane rich stage, of structural units of a vinyl monomer; and 10 to 100 wt %, based on weight of the carbosiloxane rich stage, of structural units of a second carbosiloxane monomer of formula (I); wherein the first carbosiloxane monomer of formula (I) and the second carbosiloxane monomer of formula (I) are the same or different; and (C) an antiperspirant aluminum salt;

wherein the aqueous antiperspirant composition is an emulsion.

2. The aqueous antiperspirant composition of claim 1, wherein the antiperspirant aluminum salt is selected from the group consisting of an aluminum halohydrate, an aluminum zirconium halohydrate, a complex of zirconium hydroxychloride with an amino acid, a complex of aluminum hydroxychloride with an amino acid, and mixtures thereof.

3. The aqueous antiperspirant composition of claim 2, wherein the antiperspirant aluminum salt includes an aluminum chlorohydrate.

4. The aqueous antiperspirant composition of claim 3, further comprising:

an oil, wherein the oil is selected from the group consisting of volatile silicone oils, nonvolatile silicone oils, hydrocarbon oils and mixtures thereof; and wherein the aqueous antiperspirant composition is a water-in-oil emulsion.

5. The aqueous antiperspirant composition of claim 3, further comprising:

a fragrance; and a nonionic surfactant of formula (VI)

(VI)

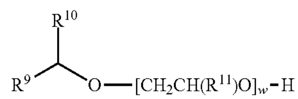

wherein w is an average of 5 to 60; wherein $R^9$ is selected from the group consisting of a hydrogen and a linear or branched $C_{1-20}$ alkyl group; wherein $R^{10}$ is selected from the group consisting of a linear or branched $C_{1-20}$ alkyl group and a linear or branched $C_{1-4}$ hydroxyalkyl group; wherein each $R^{11}$ is independently selected from the group consisting of a hydrogen, a methyl group, an ethyl group, a n-propyl group, an iso-propyl group, a n-butyl group, a 2-butyl group and a 2-methyl-2-butyl group; and with the proviso that sum of the total number of carbon atoms in $R^9$ and $R^{10}$ is 5 to 21;

wherein the aqueous antiperspirant composition is an oil-in-water emulsion.

6. The aqueous antiperspirant composition of claim 5, wherein the nonionic surfactant of formula (VI) is of formula (VIa)

(VIa)

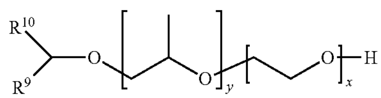

wherein x is an average of 5 to 60; wherein y is an average of 0 to 15; wherein $R^9$ is selected from the group consisting of a hydrogen and a linear or branched $C_{1-20}$ alkyl group; wherein $R^{10}$ is selected from the group consisting of a linear or branched $C_{1-20}$ alkyl group and a linear or branched $C_{1-4}$ hydroxyalkyl group; and with the proviso that the sum of the total number of carbon atoms in $R^9$ and $R^{10}$ is 5 to 21.

7. The aqueous antiperspirant composition of claim 6, wherein x is an average of 35 to 45; wherein y is 0; wherein $R^9$ is a linear $C_{1-15}$ alkyl group; wherein $R^{10}$ is a linear $C_{1-15}$ alkyl group; and with the proviso that the sum of the total number of carbon atoms in $R^9$ and $R^{10}$ is 11 to 16 carbon atoms.

8. A method of inhibiting perspiration, comprising:

providing water;

providing an antiperspirant aluminum salt;

selecting a sweat repellent polymer, wherein the sweat repellent polymer is selected to have a sweat contact angle of ≥30° and wherein the sweat repellent polymer comprises a multistage polymer comprising:

(a) an acrylate rich stage comprising:

38 to <100 wt %, based on weight of the acrylate rich stage, of structural units of a monoethylenically unsaturated nonionic acrylate rich stage monomer, wherein the monoethylenically unsaturated nonionic acrylate rich stage monomer is selected from the group consisting of $C_{1-22}$ alkyl (meth)acrylates and mixtures thereof;

>0 to 50 wt %, based on weight of the acrylate rich stage, of structural units of a first carbosiloxane monomer of formula (I)

(I)

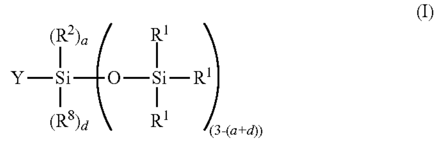

wherein a is 1; wherein d is 0; wherein each $R^1$ is independently selected from the group consisting of a hydrogen, a $C_{1-10}$ alkyl group and an aryl group; wherein each $R^2$ is independently selected from the group consisting of a hydrogen and a $C_{1-10}$ alkyl group; wherein each $R^8$ is a $—O—Si(CH_3)_3$ group; wherein Y is selected from the group consisting of formulas (II), (III) and (IV)

(II)

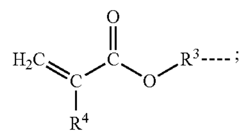

(III)

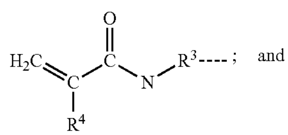

-continued (IV)

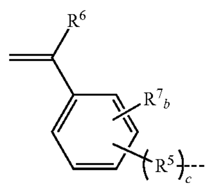

wherein each $R^4$ and $R^6$ are independently selected from the group consisting of a hydrogen and a methyl group; wherein each $R^3$ and $R^5$ are independently a $C_{1-10}$ alkylene group; wherein each $R^7$ is independently a $C_{1-10}$ alkyl group; wherein b is 0 to 4; wherein c is 0 or 1;

0 to 10 wt %, based on weight of the acrylate rich stage, of structural units of a monoethylenically unsaturated carboxylic acid acrylate rich stage monomer; and 0 to 2 wt %, based on weight of the acrylate rich stage, of structural units of a multiethylenically unsaturated acrylate rich stage monomer having at least two ethylenically unsaturated groups per molecule; and (b) a carbosiloxane rich stage, comprising:

0 to 90 wt %, based on weight of the carbosiloxane rich stage, of structural units of a vinyl monomer; and 10 to 100 wt %, based on weight of the carbosiloxane rich stage, of structural units of a second carbosiloxane monomer of formula (I); wherein the first carbosiloxane monomer of formula (I) and the second carbosiloxane monomer of formula (I) are the same or different; and providing the selected sweat repellent polymer;

combining the water, the antiperspirant aluminum salt and the selected sweat repellent polymer to form an aqueous antiperspirant composition; wherein the aqueous antiperspirant composition is an emulsion; and applying the aqueous antiperspirant composition on skin to form a film.

9. The method of claim 8, further comprising:

providing a fragrance;

providing a nonionic surfactant of formula (VI)

(VI)

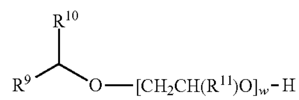

wherein w is an average of 5 to 60; wherein $R^9$ is selected from the group consisting of a hydrogen and a linear or branched $C_{1-20}$ alkyl group; wherein $R^{10}$ is selected from the group consisting of a linear or branched $C_{1-20}$ alkyl group and a linear or branched $C_{1-4}$ hydroxyalkyl group; wherein each $R^{11}$ is independently selected from the group consisting of a hydrogen, a methyl group, an ethyl group, a n-propyl group, an iso-propyl group, a n-butyl group, a 2-butyl group and a 2-methyl-2-butyl group; and with the proviso that sum of the total number of carbon atoms in $R^9$ and $R^{10}$ is 5 to 21; and combining the fragrance and the nonionic surfactant of formula (VI) with the water, the antiperspirant aluminum salt and the selected sweat repellent polymer to form the aqueous antiperspirant composition; wherein the aqueous antiperspirant composition is an oil-in-water emulsion; and wherein fragrance is released when the film is exposed to perspiration.

10. The method of claim 9, wherein the nonionic surfactant of formula (VI) provided is of formula (VIa)

(VIa)

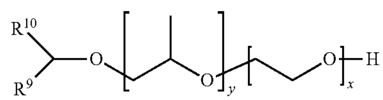

wherein x is an average of 35 to 45; wherein y is 0; wherein $R^9$ is a linear $C_{1-15}$ alkyl group; wherein $R^{10}$ is selected a linear $C_1$-15 alkyl group; and with the proviso that the sum of the total number of carbon atoms in $R^9$ and $R^{10}$ is 11 to 16.

* * * * *